United States Patent
Ebens, Jr. et al.

(10) Patent No.: US 6,913,899 B2
(45) Date of Patent: Jul. 5, 2005

(54) POLYNUCLEOTIDES ENCODING INSECT ETHANOLAMINE KINASE AND USES THEREOF

(75) Inventors: Allen J. Ebens, Jr., San Carlos, CA (US); Stuart Johnston, Menlo Park, CA (US); Jean-Claude Breach, San Francisco, CA (US)

(73) Assignee: Genoptera, LLC, South San Francisco, CA (US)

( * ) Notice: Subject to any disclaimer, the term of this patent is extended or adjusted under 35 U.S.C. 154(b) by 0 days.

(21) Appl. No.: 10/194,125

(22) Filed: Jul. 11, 2002

(65) Prior Publication Data

US 2003/0027191 A1 Feb. 6, 2003

Related U.S. Application Data

(60) Provisional application No. 60/306,496, filed on Jul. 18, 2001.

(51) Int. Cl.$^7$ .......................... C12Q 1/48; C12N 9/12; A61K 31/00
(52) U.S. Cl. .................. 435/15; 435/194; 514/789
(58) Field of Search .................... 435/15, 194; 514/789

(56) References Cited

PUBLICATIONS

Blocks Database, entry IPB002573, http://blocks.fhcrc.org/blocks-bin/getblock.sh?IPB002573, Oct. 2003.*

C.A. Wilson et al. "Assessing Annotation Transfer for Genomics: Quantifying the Relations Between Protein Sequence, Structure and Function Through Traditional and Probalistic Scores.", J. Mol. Biol. 297: 233–249 (2000).*

Uchida, Tsutomu "A Novel High–Molecular Mass Mammalian Ethanolamine Kinase", Biochimica et Biophysica Acta, vol. 1349, No. 1, Nov. 8, 1997.

Pavlidis, P, et al., "Easily shocked protein–fruit fly (*Drosophila malanogaster*)", Genbank accession No.: A54980, (Jul. 2000).

Wiedmer, T, et al., "Homo sapiens phospholipid scramblase 1 gene, complete eds", Genbank accession No.: AF224492, (Aug. 2000).

Pavlidis et al., (1994), *Cell*, 79:23–33.

Pavlidis et al., (1995), *J. Neurosci.*, 15:5810–5819.

Porter et al., (1990), *J. Biol. Chem.*, 265:414–422.

Kim et al., (1999), *J. Biol. Chem.*, 274:14857–14866.

Draus et al., (1990), *Biochim. Biophys. Acta*, 1045:195–205.

Ishidate, (1997), *Biochim. Biophys. Acta*, 1348:70–78.

\* cited by examiner

*Primary Examiner*—Rebecca Prouty
(74) *Attorney, Agent, or Firm*—Paula A. Borden; Bozicevic, Field & Francis, LLP

(57) ABSTRACT

The instant invention provides nucleic acid molecules encoding insect ethanolamine kinase, as well as ethanolamine kinase encoded thereby. The invention further provides methods of identifying agents that modulate a level of ethanolamine kinase mRNA, polypeptide, or enzyme activity. Such agents are candidate insecticidal compounds.

4 Claims, 3 Drawing Sheets

FIG. 1

Heliothis Ethanolamine kinase cDNA Alt1-long

```
CCCTGGCGCCCAATACGCAAACCGCCTCTCCCCGCGCGTTGGCCGATTCATTAATGCAGCTGGCACGACA
GGTTTCCCGACTGGAAAGCGGGCAGTGAGCGCAACGCAATTAATGTGAGTTAGCTCACTCATTAGGCACC
CCAGGCTTTACACTTTATGCTTCCGGCTCGTATGTTGTGTGGAATTGTGAGCGGATAACAATTTCACACA
GGAAACAGCTATGACCATGATTACGCCAAGCTCTAATACGACTCACTATAGGGAAAGCTGGTACGCCTGC
AGGTACCGGTCCGGAATTCCCGGGTCGACCAATGCCACGCGTCCGAAAAGATTCGGTCAACTCAAGCTGT
AAAACTCAGCGTACTTGTTCTATCCGATCATACTTGTTATTTAGTATTTTTTATTTAATCAAATTTAC
TGCCGGAATAAATAAAACTATTTTACACTATAGGGTGCTTTCAAACATTTATATAGTTTGTAAATAATAT
CACTATTGAAGTACTTTCAGCACTAACAGTAATAAATATTTTATTAATTAAATTACAAAGTAAGTTATGT
CGTCTGTTTGCCCCGCCGCTGGAGATATATTCGTGCCAGTTAAAATTGATGAAAATGATATTTATGCTGG
TGTATTTAAACTTCTTAAAAATATAAGACCAAACTGGACTAAAGAAAATATTAAACTTAAGACTCTTACA
GATGGAATTACTAATAAGTTAGTATCTTGTCAATATTTGGAAGCAAATGGAAAACAAGACATTCTGCTGG
TTCGCATTTATGGAAACAAAACTGACTTATTTATTGATCGTACGGCTGAAATCAGGAACATCAAAACTCT
TAATGTGCTTGGCTTAGCACCTGAAGTTTATGGAATATTTGAGAATGGACTTGCTTACCAATATTATCCA
GGAATTACGTTGGATGTTGAATCAGTTAAAAATAATAATATATGGCCGCTAGTGGCAACACAAATGGCAA
AAATGCACAAAGTTGAACTCGGAAAAGATGTACCGAAAGAGCCATTTGTTTGGGATAAGATTGAACAATT
TTTGAGTTTGTTGCCCGATCCGTATTCGTCAGAGGATAAGCAAGCCAGATTCACAAATAGTTTCAGCTCG
TTAACAAAACTAAGGATAGAGTACGAGCGTCTTAAATCGCACCTATCACAAACTAAAAGTCCTGTTGTGT
TTGCTCACAATGATTTGCTTCTAGGAAACGTAATTTACAACAAAGATGAAGGTACAATATCTTTCATTGA
TTATGAATACGCTGCGTACTGCTATCAAGCTTCGATATAGCCAATCACTTCAATGAGTTCGTTGGGATT
TCTCTGGAAGACATCGATTACGACAAATATCCCTGCGAAGAATTTCAGTTGGAGTGGATCAAAGTATATC
TAGCTATATACTTGGATATAGACCATCCTTCTGATCCGCTCATATATAAAGTATATACAGAAGTTCAGGA
AATGTCATTGCTGTCTCATTTCCTTTGGGGAATATGGTCACTTGTACAGTATGAACATTCAGATATCGAC
TTCGATTTTGGAAGATATGCTGAAATAAGATTGAACAGATATTTTGAGCTAAAAGATAAGATCTTCAAGC
AACGAAGTTGACTGAACGTTATTTAGGTAGCTATCGAGAGGCTCATTCATGTTAATCGCTAATCTAAAAT
AAGATGTAAAATTATGTTATATGTATAGTTCATAGAGTTAAGATCGATGGAAAAGTACAATTATTATAAA
AAGTAGAGAAAAATATTAATTTTAAAGCATTGCTTAGCGATGCTGTATTAAGGATACTACTTACCTTCTT
ATTTATAAAAATACCTACATTCCTAATTATATTTTTCTGTAAGTATTTGTTTATAATATATGTTCATTT
GTATGTAGAAATAAGAGCATGGTTATTAATTTAATATACCTACTATTAAAAGATTTAAATAGTCAAAAAA
AAAAAAAAAAAAAAAAAAAAGGCCATTGCGGCCGCTCTAGAGGATCCAAGCTTACGTACGCGTGCATGCA
CGTCATAGCTCTTCTATAGTGTCACCTAAATTCAATTCACTGGCCGTCGTTTTACAACGTCGTGACTGGG
AAAACCCTGGCGTTACCCAACTTAATCGCCTTGCAGCACATCCCCCTTTCGCCAGCTGGCGTAATAGCGA
AGAGGCCCGCACCGATCGCCCTTCCCAACAGTTGCGCAGCCTGAATGGCGAATGGGACGCGCCCTGTAGC
GGCGCATTAAGCGCGGCGGGTGTGGTGGTTACGCGCAGCGTGACCGCTACACTTGCCAGCGCCCTAGCGC
CCGCTCCTTTCGCTTTCTTCCCTTCCTTTCTCGCCACGTTCGCCGGCTTTCCCCGTCAAGCTCTAAATCG
GGGGCTCCCTTTAGGGTTCCGA
```

FIG. 2

Heliothis Ethanolamine kinase predicted peptide Alt1-long(nt 557-1618)

MSSVCPAAGDIFVPVKIDENDIYAGVFKLLKNIRPNWTKENIKLKTLTDGITNKLVSCQYLE
ANGKQDILLVRIYGNKTDLFIDRTAEIRNIKTLNVLGLAPEVYGIFENGLAYQYYPGITLDV
ESVKNNNIWPLVATQMAKMHKVELGKDVPKEPFVWDKIEQFLSLLPDPYSSEDKQARFTNSF
SSLTKLRIEYERLKSHLSQTKSPVVFAHNDLLLGNVIYNKDEGTISFIDYEYAAYCYQAFDI
ANHFNEFVGISLEDIDYDKYPCEEFQLEWIKVYLAIYLDIDHPSDPLIYKVYTEVQEMSLLS
HFLWGIWSLVQYEHSDIDFDFGRYAEIRLNRYFELKDKIFKQRS

FIG. 3

Heliothis Ethanolamine kinase cDNA Alt2-short

```
CCGCCTCTCCCCGCGCGTTGGCCGATTCATTAATGCAGCTGGCACGACAGGTTTCCCGACTGGAAAGCGGG
CAGTGAGCGCAACGCAATTAATGTGAGTTAGCTCACTCATTAGGCACCCCAGGCTTTACACTTTATGCTTC
CGGCTCGTATGTTGTGTGGAATTGTGAGCGGATAACAATTTCACACAGGAAACAGCTATGACCATGATTAC
GCCAAGCTCTAATACGACTCACTATAGGGAAAGCTGGTACGCCTGCAGGTACCGGTCCGGAATTCCCGGGT
CGACCAATGCCACGCGTCCGAAAAGATTCGGTCAACTCAAGCTGTAAAACTCAGCGTACTTGTTCTATCCG
ATCATACTTGTTATTTAGTATTTTTTTATTTAATCAAAATTTACTGCCGGAATAAATAAAACTATTTTACA
CTATAGGGTGCTTTCAAACATTTATATAGTTTGTAAATAATATCACTATTGAAGTACTTTCAGCACTAACA
GTAATAAATATTTTATTAATTAAATTACAAAGTAAGTTATGTCGTCTGTTTGCCCCGCCGCTGGAGATATA
TTCGTGCCAGTTAAAATTGATGAAAATGATATTTATGCTGGTGTATTTAAACTTCTTAAAAATATAAGACC
AAACTGGACTAAAGAAAATATTAAACTTAAGACTCTTACAGATGGAATTACTAATAAGTTAGTATCTTGTC
AATATTTGGAAGCAAATGGAAAACAAGACATTCTGCTGGTTCGCATTTATGGAAACAAAACTGACTTATTT
ATTGATCGTACGGCTGAAATCAGGAACATCAAAACTCTTAATGTGCTTGGCTTAGCACCTGAAGTTTATGG
AATATTTGAGAATGGACTTGCTTACCAATATTATCCAGGAATTACGTTGGATGTTAATCAGTTAAAAATA
ATAATATATGGCCGCTAGTGGCAACACAAATGGCAAAAATGCACAAAGTTGAACTCGGAAAAGATGTACCG
AAAGAGCCATTTGTTTGGGATAAGATTGAACAATTTTTGAGTTTGTTGCCCGATCCGTATTCGTCAGAGGA
TAAGCAAGCCAGATTCACAAATAGTTTCAGCTCGTTAACAAAACTAAGGATAGAGTACGAGCGTCTTAAAT
CGCACCTATCACAAACTAAAAGTCCTGTTGTGTTTGCTCACAATGATTTGCTTCTAGGAAACGTAATTTAC
AACAAAGATGAAGGGATTTCTCTGGAAGACATCGATTACGACAAATATCCCTGCGAAGAATTTCAGTTGGA
GTGGATCAAAGTATATCTAGCTATATACTTGCATATAGACCATCCTTCTGATCCGCTCATATATAAAGTAT
ATACAGAAGTTCAGGAAATGTCATTGCTGTCTCATTTCCTTTGGGGAATATGGTCACTTGTACAGTATGAA
CATTCAGATATCGACTTCGATTTTGGAAGATATGCGGAAATAAGATTGAACAGATATTTTGAGCTAAAAGA
TAAGATCTTCAAGCAACTAAGTTGACTGACCGTTATTAGGTAGCTATCGAGAGGCTCATTCATGTTAATC
GCTAATCTAAAATAAGATGTAAAATTATGTTATATAGTTCATAGAGTTAAGATCGATGGAAAAGTACAATT
ATTATAAAAAGTAGAGAAAAATATTAATTTTAAAGTATTGCTTAGCGATGCTGTATTAAGGATACTACTTA
CCTTCTTATTTATAAAAATACCTACATTCCTAATTATATTTTTTCTGTAAGTATTTGTTTGTAATATATGT
TCATTTGTATGTAGAAATAAGAGCATGGTTATTAATTTAATATACCTACTATTAAAAGATTTAAATAGTCA
AAAAAAAAAAAAAAAAAAAAAAAAGGGCATGGCGGCCGCTCTAGAGGATCCAAGCTTACGTACGCGTGCAT
GCGACGTCATAGCTCTTCTATAGTGTCACCTAAATTCAATTCACTGGCCGTCGTTTTACAACGTCGTGACT
GGGAAAACCCTGGCGTTACCCAACTTAATCGCCTTGCAGCACATCCCCCTTTCGCCAGCTGGCGTAATAGC
GAAGAGGCCCGCACCGATCGCCCTTCCCAACAGTTGCGCAGCCTGAATGGCGAATGGGACGCGCCCTGTAG
CGGCGCATTAAGCGCGGCGGGTGTGGTGGTTACGCGCAGCGTGACCGCTACACTTGCCAGCGCCCTAGCGC
CCGCTCCTTTCGCTTTCTTCCCTTCCTTTCTCGCCACGTTCGCCGGCTTTCCCCGTCAAGCTCTAAATCGG
GGGCTCCCTTTAGGGTTCCGATTTAGTGCTTTACGGCACCTCGACCCCAA
```

FIG. 4

Heliothis Ethanolamine kinase predicted peptide Alt2-short(nt536-1513)

```
MSSVCPAAGDIFVPVKIDENDIYAGVFKLLKNIRPNWTKENIKLKTLTDGITNKLVSCQYLEANGKQDILL
VRIYGNKTDLFIDRTAEIRNIKTLNVLGLAPEVYGIFENGLAYQYYPGITLDVESVKNNNIWPLVATQMAK
MHKVELGKDVPKEPFVWDKIEQFLSLLPDPYSSEDKQARFTNSFSSLTKLRIEYERLKSHLSQTKSPVVFA
HNDLLLGNVIYNKDEGISLEDIDYDKYPCEEFQLEWIKVYLAIYLDIDHPSDPLIYKVYTEVQEMSLLSHF
LWGIWSLVQYEHSDIDFDFGRYAEIRLNRYFELKDKIFKQLS
``` ated enzyme may have utility

SEQUENCE LISTING

```
<160> NUMBER OF SEQ ID NOS: 5

<210> SEQ ID NO 1
<211> LENGTH: 2402
<212> TYPE: DNA
<213> ORGANISM: Heliothis virescens
```

-continued

```
<400> SEQUENCE: 1
ccctggcgcc caatacgcaa accgcctctc cccgcgcgtt ggccgattca ttaatgcagc     60
tggcacgaca ggtttcccga ctggaaagcg ggcagtgagc gcaacgcaat taatgtgagt    120
tagctcactc attaggcacc ccaggcttta cactttatgc ttccggctcg tatgttgtgt    180
ggaattgtga gcggataaca atttcacaca ggaaacagct atgaccatga ttacgccaag    240
ctctaatacg actcactata gggaaagctg gtacgcctgc aggtaccggt ccggaattcc    300
cgggtcgacc aatgccacgc gtccgaaaag attcggtcaa ctcaagctgt aaaactcagc    360
gtacttgttc tatccgatca tacttgttat ttagtatttt tttatttaat caaaatttac    420
tgccggaata aataaaacta ttttacacta tagggtgctt tcaaacatttt atatagtttg    480 taaataatat cactattgaa gtactttcag cactaacagt aataaatatt ttattaatta    540
aattacaaag taagttatgt cgtctgtttg ccccgccgct ggagatatat cgtgccagt     600 taaaattgat gaaaatgata tttatgctgg tgtatttaaa cttcttaaaa atataagacc    660
aaactggact aagaaaata ttaaacttaa gactcttaca gatggaatta ctaataagtt    720
agtatcttgt caatatttgg aagcaaatgg aaaacaagac attctgctgg ttcgcattta    780
tggaaacaaa actgacttat ttattgatcg tacggctgaa atcaggaaca tcaaaactct    840
taatgtgctt ggcttagcac ctgaagttta tggaatattt gagaatggac ttgcttacca    900
atattatcca ggaattacgt tggatgttga atcagttaaa aataataata tatggccgct    960
agtggcaaca caaatggcaa aaatgcacaa agttgaactc ggaaaagatg taccgaaaga   1020
gccatttgtt tgggataaga ttgaacaatt tttgagtttg ttgcccgatc cgtattcgtc   1080
agaggataag caagccagat tcacaaatag tttcagctcg ttaacaaaac taaggataga   1140
gtacgagcgt cttaaatcgc acctatcaca aactaaaagt cctgttgtgt ttgctcacaa   1200
tgatttgctt ctaggaaacg taatttacaa caaagatgaa ggtacaatat ctttcattga   1260
ttatgaatac gctgcgtact gctatcaagc tttcgatata gccaatcact tcaatgagtt   1320
cgttgggatt tctctggaag acatcgatta cgacaaatat ccctgcgaag aatttcagtt   1380
ggagtggatc aaagtatatc tagctatata cttggatata gaccatcctt ctgatccgct   1440
catatataaa gtatacag aagttcagga aatgtcattg ctgtctcatt tcctttgggg     1500
aatatggtca cttgtacagt atgaacattc agatatcgac ttcgattttg gaagatatgc   1560
tgaaataaga ttgaacagat attttgagct aaaagataag atcttcaagc aacgaagttg   1620
actgaacgtt atttaggtag ctatcgagag gctcattcat gttaatcgct aatctaaaat   1680
aagatgtaaa attatgttat atgtatagtt catagagtta agatcgatgg aaaagtacaa   1740
ttattataaa aagtagagaa aaatattaat tttaaagcat tgcttagcga tgctgtatta   1800
aggatactac ttaccttctt atttataaaa atacctacat tcctaattat atttttctg    1860 taagtatttg tttataatat atgttcattt gtatgtagaa ataagagcat ggttattaat   1920
ttaatatacc tactattaaa agatttaaat agtcaaaaaa aaaaaaaaaa aaaaaaaag    1980 gccattgcgg ccgctctaga ggatccaagc ttacgtacgg gtgcatgcga cgtcatagct   2040
cttctatagt gtcacctaaa ttcaattcac tggccgtcgt tttacaacgt cgtgactggg   2100
aaaaccctgg cgttacccaa cttaatcgcc ttgcagcaca tcccccttc gccagctggc    2160 gtaatagcga agaggcccgc accgatcgcc cttcccaaca gttgcgcagc ctgaatggcg   2220
aatgggacgc gccctgtagc ggcgcattaa gcgcggcggg tgtggtggtt acgcgcagcg   2280
tgaccgctac acttgccagc gccctagcgc ccgctccttt cgctttcttc ccttcctttc   2340
```

```
tcgccacgtt cgccggcttt ccccgtcaag ctctaaatcg ggggctccct ttagggttcc    2400
ga                                                                  2402
```

<210> SEQ ID NO 2
<211> LENGTH: 354
<212> TYPE: PRT
<213> ORGANISM: Heliothis virescens

<400> SEQUENCE: 2

```
Met Ser Ser Val Cys Pro Ala Ala Gly Asp Ile Phe Val Pro Val Lys
  1               5                  10                  15

Ile Asp Glu Asn Asp Ile Tyr Ala Gly Val Phe Lys Leu Leu Lys Asn
             20                  25                  30

Ile Arg Pro Asn Trp Thr Lys Glu Asn Ile Lys Leu Lys Thr Leu Thr
         35                  40                  45

Asp Gly Ile Thr Asn Lys Leu Val Ser Cys Gln Tyr Leu Glu Ala Asn
 50                  55                  60

Gly Lys Gln Asp Ile Leu Leu Val Arg Ile Tyr Gly Asn Lys Thr Asp
 65                  70                  75                  80

Leu Phe Ile Asp Arg Thr Ala Glu Ile Arg Asn Ile Lys Thr Leu Asn
                 85                  90                  95

Val Leu Gly Leu Ala Pro Glu Val Tyr Gly Ile Phe Glu Asn Gly Leu
            100                 105                 110

Ala Tyr Gln Tyr Tyr Pro Gly Ile Thr Leu Asp Val Glu Ser Val Lys
        115                 120                 125

Asn Asn Asn Ile Trp Pro Leu Val Ala Thr Gln Met Ala Lys Met His
130                 135                 140

Lys Val Glu Leu Gly Lys Asp Val Pro Lys Glu Pro Phe Val Trp Asp
145                 150                 155                 160

Lys Ile Glu Gln Phe Leu Ser Leu Leu Pro Asp Pro Tyr Ser Ser Glu
                165                 170                 175

Asp Lys Gln Ala Arg Phe Thr Asn Ser Phe Ser Ser Leu Thr Lys Leu
            180                 185                 190

Arg Ile Glu Tyr Glu Arg Leu Lys Ser His Leu Ser Gln Thr Lys Ser
        195                 200                 205

Pro Val Val Phe Ala His Asn Asp Leu Leu Leu Gly Asn Val Ile Tyr
210                 215                 220

Asn Lys Asp Glu Gly Thr Ile Ser Phe Ile Asp Tyr Glu Tyr Ala Ala
225                 230                 235                 240

Tyr Cys Tyr Gln Ala Phe Asp Ile Ala Asn His Phe Asn Glu Phe Val
                245                 250                 255

Gly Ile Ser Leu Glu Asp Ile Asp Tyr Asp Lys Tyr Pro Cys Glu Glu
            260                 265                 270

Phe Gln Leu Glu Trp Ile Lys Val Tyr Leu Ala Ile Tyr Leu Asp Ile
        275                 280                 285

Asp His Pro Ser Asp Pro Leu Ile Tyr Lys Val Tyr Thr Glu Val Gln
290                 295                 300

Glu Met Ser Leu Leu Ser His Phe Leu Trp Gly Ile Trp Ser Leu Val
305                 310                 315                 320

Gln Tyr Glu His Ser Asp Ile Asp Phe Asp Phe Gly Arg Tyr Ala Glu
                325                 330                 335

Ile Arg Leu Asn Arg Tyr Phe Glu Leu Lys Asp Lys Ile Phe Lys Gln
            340                 345                 350

Arg Ser
```

<210> SEQ ID NO 3
<211> LENGTH: 2322
<212> TYPE: DNA
<213> ORGANISM: Heliothis virescens

<400> SEQUENCE: 3
ccgcctctcc ccgcgcgttg gccgattcat taatgcagct ggcacgacag gtttcccgac 60
tggaaagcgg gcagtgagcg caacgcaatt aatgtgagtt agctcactca ttaggcaccc 120
caggctttac actttatgct tccggctcgt atgttgtgtg gaattgtgag cggataacaa 180
tttcacacag gaaacagcta tgaccatgat tacgccaagc tctaatacga ctcactatag 240
ggaaagctgg tacgcctgca ggtaccggtc cggaattccc gggtcgacca atgccacgcg 300
tccgaaaaga ttcggtcaac tcaagctgta aaactcagcg tacttgttct atccgatcat 360
acttgttatt tagtattttt ttatttaatc aaaatttact gccggaataa ataaaactat 420
tttacactat agggtgcttt caaacattta tatagtttgt aaataatatc actattgaag 480
tactttcagc actaacagta ataaatattt tattaattaa attacaaagt aagttatgtc 540
gtctgtttgc cccgccgctg gagatatatt cgtgccagtt aaaattgatg aaaatgatat 600
ttatgctggt gtatttaaac ttcttaaaaa tataagacca aactggacta aagaaaatat 660
taaacttaag actcttacag atggaattac taataagtta gtatcttgtc aatatttgga 720
agcaaatgga aaacaagaca ttctgctggt tcgcatttat ggaaacaaaa ctgacttatt 780
tattgatcgt acggctgaaa tcaggaacat caaaactctt aatgtgcttg gcttagcacc 840
tgaagtttat ggaatatttg agaatggact tgcttaccaa tattatccag gaattacgtt 900
ggatgttgaa tcagttaaaa ataataatat atggccgcta gtggcaacac aaatggcaaa 960
aatgcacaaa gttgaactcg gaaaagatgt accgaaagag ccatttgttt gggataagat 1020
tgaacaattt ttgagtttgt tgcccgatcc gtattcgtca gaggataagc aagccagatt 1080
cacaaatagt ttcagctcgt taacaaaact aaggatagag tacgagcgtc ttaaatcgca 1140
cctatcacaa actaaaagtc ctgttgtgtt tgctcacaat gatttgcttc taggaaacgt 1200
aatttacaac aaagatgaag ggatttctct ggaagacatc gattacgaca aatatccctg 1260
cgaagaattt cagttggagt ggatcaaagt atatctagct atatacttgg atatagacca 1320
tccttctgat ccgctcatat ataaagtata tacagaagtt caggaaatgt cattgctgtc 1380
tcatttcctt tggggaatat ggtcacttgt acagtatgaa cattcagata tcgacttcga 1440
ttttggaaga tatgcggaaa taagattgaa cagatatttt gagctaaaag ataagatctt 1500
caagcaacta agttgactga ccgttattta ggtagctatc gagaggctca ttcatgttaa 1560
tcgctaatct aaaataagat gtaaaattat gttatatagt tcatagagtt aagatcgatg 1620
gaaaagtaca attattataa aaagtagaga aaaatattaa ttttaaagta ttgcttagcg 1680
atgctgtatt aaggatacta cttaccttct tatttataaa aatacctaca ttcctaatta 1740
tattttttct gtaagtattt gtttgtaata tatgttcatt tgtatgtaga aataagagca 1800
tggttattaa tttaatatac ctactattaa aagatttaaa tagtcaaaaa aaaaaaaaaa 1860
aaaaaaaaaa gggcatggcg gccgctctag aggatccaag cttacgtacg cgtgcatgcg 1920
acgtcatagc tcttctatag tgtcacctaa attcaattca ctggccgtcg ttttacaacg 1980
tcgtgactgg gaaaaccctg gcgttaccca acttaatcgc cttgcagcac atcccccttt 2040
cgccagctgg cgtaatagcg aagaggcccg caccgatcgc ccttcccaac agttgcgcag 2100
cctgaatggc gaatgggacg cgccctgtag cggcgcatta agcgcggcgg gtgtggtggt 2160

-continued

```
tacgcgcagc gtgaccgcta cacttgccag cgccctagcg cccgctcctt tcgctttctt      2220
cccttccttt ctcgccacgt tcgccggctt tccccgtcaa gctctaaatc gggggctccc      2280
tttagggttc cgatttagtg ctttacggca cctcgacccc aa                         2322
```

<210> SEQ ID NO 4
<211> LENGTH: 326
<212> TYPE: PRT
<213> ORGANISM: Heliothis virescens

<400> SEQUENCE: 4

```
Met Ser Ser Val Cys Pro Ala Ala Gly Asp Ile Phe Val Pro Val Lys
 1               5                  10                  15

Ile Asp Glu Asn Asp Ile Tyr Ala Gly Val Phe Lys Leu Leu Lys Asn
             20                  25                  30

Ile Arg Pro Asn Trp Thr Lys Glu Asn Ile Lys Leu Lys Thr Leu Thr
         35                  40                  45

Asp Gly Ile Thr Asn Lys Leu Val Ser Cys Gln Tyr Leu Glu Ala Asn
     50                  55                  60

Gly Lys Gln Asp Ile Leu Leu Val Arg Ile Tyr Gly Asn Lys Thr Asp
 65                  70                  75                  80

Leu Phe Ile Asp Arg Thr Ala Glu Ile Arg Asn Ile Lys Thr Leu Asn
                 85                  90                  95

Val Leu Gly Leu Ala Pro Glu Val Tyr Gly Ile Phe Glu Asn Gly Leu
            100                 105                 110

Ala Tyr Gln Tyr Tyr Pro Gly Ile Thr Leu Asp Val Glu Ser Val Lys
        115                 120                 125

Asn Asn Asn Ile Trp Pro Leu Val Ala Thr Gln Met Ala Lys Met His
    130                 135                 140

Lys Val Glu Leu Gly Lys Asp Val Pro Lys Glu Pro Phe Val Trp Asp
145                 150                 155                 160

Lys Ile Glu Gln Phe Leu Ser Leu Leu Pro Asp Pro Tyr Ser Ser Glu
                165                 170                 175

Asp Lys Gln Ala Arg Phe Thr Asn Ser Phe Ser Ser Leu Thr Lys Leu
            180                 185                 190

Arg Ile Glu Tyr Glu Arg Leu Lys Ser His Leu Ser Gln Thr Lys Ser
        195                 200                 205

Pro Val Val Phe Ala His Asn Asp Leu Leu Gly Asn Val Ile Tyr
    210                 215                 220

Asn Lys Asp Glu Gly Ile Ser Leu Glu Asp Ile Asp Tyr Asp Lys Tyr
225                 230                 235                 240

Pro Cys Glu Glu Phe Gln Leu Glu Trp Ile Lys Val Tyr Leu Ala Ile
                245                 250                 255

Tyr Leu Asp Ile Asp His Pro Ser Asp Pro Leu Ile Tyr Lys Val Tyr
            260                 265                 270

Thr Glu Val Gln Glu Met Ser Leu Leu Ser His Phe Leu Trp Gly Ile
        275                 280                 285

Trp Ser Leu Val Gln Tyr Glu His Ser Asp Ile Asp Phe Asp Phe Gly
    290                 295                 300

Arg Tyr Ala Glu Ile Arg Leu Asn Arg Tyr Phe Glu Leu Lys Asp Lys
305                 310                 315                 320

Ile Phe Lys Gln Leu Ser
                325
```

```
-continued

<210> SEQ ID NO 5
<211> LENGTH: 28
<212> TYPE: PRT
<213> ORGANISM: Heliothis virescens

<400> SEQUENCE: 5

Thr Ile Ser Phe Ile Asp Tyr Glu Tyr Ala Ala Tyr Cys Tyr Gln Ala
1               5                   10                  15

Phe Asp Ile Ala Asn His Phe Asn Glu Phe Val Gly
            20                  25
```

POLYNUCLEOTIDES ENCODING INSECT ETHANOLAMINE KINASE AND USES THEREOF This application claims benefit of 60/306,496, filed Jul. 18, 2001.

FIELD OF THE INVENTION

The invention relates to insect enzymes, and in particular to an insect ethanolamine kinase.

BACKGROUND OF THE INVENTION

The phospholipids phosphatidylethanolamine and phosphatidyl choline are the primary phospholipids comprising cellular membranes. Phosphatidylethanolamine is the predominant lipid in *Drosophila*. Lipid composition and its regulation affect many cellular processes including lipid-derived second messenger systems, function of membrane proteins such as ion channels, and membrane fusion and trafficking. The mechanism of these effects remains unknown. Ethanolamine kinase catalyzes the initial step in the CDP-ethanolamine pathway for phosphatidyl ethanolamine synthesis.

Pesticide development has traditionally focused on the chemical and physical properties of the pesticide itself, a relatively time-consuming and expensive process. As a consequence, efforts have been concentrated on the modification of pre-existing, well-validated compounds, rather than on the development of new pesticides. There is a need in the art for new pesticidal compounds that are safer, more selective, and more efficient than currently available pesticides. The present invention addresses this need by providing novel pesticide targets from invertebrates such as the tobacco budworm *Heliothis virescens*, and by providing methods of identifying compounds that bind to and modulate the activity of such targets.

Literature

Pavlidis et al. (1994) *Cell* 79:23–33; Pavlidis et al. (1995) *J. Neurosci.* 15:5810–5819; Porter et al. (1990) *J. Biol. Chem.* 265:414–422; Kim et al. (1999) *J. Biol. Chem.* 274:14857–14866; Draus et al. (1990) *Biochim. Biophys. Acta* 1045:195–205; Ishidate (1997) *Biochim. Biophys. Acta* 1348:70–78.

SUMMARY OF THE INVENTION

The instant invention provides nucleic acid molecules encoding insect ethanolamine kinase, as well as ethanolamine kinase encoded thereby. The invention further provides methods of identifying agents that modulate a level of ethanolamine kinase mRNA, polypeptide, or enzyme activity. Such agents are candidate insecticidal compounds.

It is an object of the invention to provide isolated insect nucleic acid molecules and proteins that are targets for pesticides. The isolated insect nucleic acid molecules provided herein are useful for producing insect proteins encoded thereby. The insect proteins are useful in assays to identify compounds that modulate a biological activity of the proteins, which assays identify compounds that may have utility as pesticides. It is an object of the present invention to provide invertebrate genes encoding enzymes that can be used in genetic screening methods to characterize pathways that such genes may be involved in, as well as other interacting genetic pathways. It is also an object of the invention to provide methods for screening compounds that interact with a subject invertebrate enzyme. Compounds that interact with a subject invertebrate enzyme may have utility as therapeutics or pesticides.

BRIEF DESCRIPTIONS OF THE DRAWINGS

FIG. 1 provides the nucleotide sequence of *Heliothis* ethanolamine kinase cDNA "long form" (SEQ ID NO:01).

FIG. 2 provides the amino acid sequence of *Heliothis* ethanolamine kinase "long form" (SEQ ID NO:02).

FIG. 3 provides the nucleotide sequence of *Heliothis* ethanolamine kinase cDNA "short form" (SEQ ID NO:03).

FIG. 4 provides the amino acid sequence of *Heliothis* ethanolamine kinase "short form" (SEQ ID NO:04).

DEFINITIONS

As used herein the term "isolated" is meant to describe a polynucleotide, a polypeptide, an antibody, or a host cell that is in an environment different from that in which the polynucleotide, the polypeptide, the antibody, or the host cell naturally occurs. As used herein, the term "substantially purified" refers to a compound (e.g., either a polynucleotide or a polypeptide or an antibody) that is removed from its natural environment and is at least 60% free, at least 75% free, or at least 90% free from other components with which it is naturally associated.

The terms "polynucleotide" and "nucleic acid molecule", used interchangeably herein, refer to a polymeric forms of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) *Nucl Acids Res.* 24:1841–1848; Chaturvedi et al. (1996) *Nucl. Acids Res.* 24:2318–2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

For hybridization probes, it may be desirable to use nucleic acid analogs, in order to improve the stability and binding affinity. A number of modifications have been described that alter the chemistry of the phosphodiester backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S-phosphorothioate, 3'-S-5'-O-phosphorothioate, 3'-CH2-5'-

O-phosphonate and 3'-NH-5'-O-phosphoroamidate. Peptide nucleic acids replace the entire phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without compromising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "host cell", as used herein, denotes microorganisms or eukaryotic cells or cell lines cultured as unicellular entities which can be, or have been, used as recipients for recombinant vectors or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation. A "recombinant host cell" is a host cell into which has been introduced a subject nucleic acid molecule or a subject recombinant vector.

By "transformation" is meant a permanent or transient genetic change induced in a cell following incorporation of new DNA (i.e., DNA exogenous to the cell). Genetic change can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a pesticidal agent" includes a plurality of such agents and reference to "the ethanolamine kinase" includes reference to one or more such kinases and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The invention is based on the observation that mutations in *Drosophila* ethanolamine kinase, are either larval lethal or are detrimental to viability of the adult animal. These mutations identify insect ethanolamine kinase as a previously unrecognized insecticidal target.

A cDNA encoding a full-length open reading frame of the ethanolamine kinase was amplified from a *Heliothis virescens* cDNA library, and sequenced in its entirety.

The present invention provides insect ethanolamine kinase nucleic acid and protein compositions, as well as methods of identifying agents that modulate the level of insect ethanolamine kinase mRNA, protein, or enzymatic activity.

Isolated Nucleic Acid Molecules of the Invention

The invention provides isolated insect nucleic acid molecules comprising nucleotide sequences of insect ethanolamine kinase, particularly nucleic acid sequences of Lepidopteran ethanolamine kinase, and more particularly nucleic acid sequences of *Heliothis virescens* ethanolamine kinase, and methods of using these nucleic acid molecules.

The present invention provides isolated nucleic acid molecules that comprise nucleotide sequences encoding insect proteins that are potential pesticide targets. The isolated nucleic acid molecules have a variety of uses, e.g., as hybridization probes, e.g., to identify nucleic acid molecules that share nucleotide sequence identity; in expression vectors to produce the polypeptides encoded by the nucleic acid molecules; and to modify a host cell or animal for use in assays described hereinbelow.

The term "isolated nucleic acid sequence", as used herein, includes the reverse complement, RNA equivalent, DNA or RNA single- or double-stranded sequences, and DNA/RNA hybrids of the sequence being described, unless otherwise indicated.

FIGS. 1–4 provide the nucleotide (SEQ ID NO:01 and SEQ ID NO:03) and amino acid (SEQ ID NO:02 and SEQ ID NO:04) sequences, respectively, of an ethanolamine kinase from *Heliothis virescens*. SEQ ID NO:01 encodes a "long form" (354 amino acids; SEQ ID NO:02), and SEQ ID NO:03 encodes a "short form" (326 amino acids; SEQ ID NO:04) of an ethanolamine kinase from *Heliothis virescens*. The short form lacks an internal 28-amino acid sequence (TISFIDYEYAAYCYQAFDIANHFNEFVG; SEQ ID NO:05) found in the long form.

In some embodiments, an insect ethanolamine kinase nucleic acid molecule comprises a nucleotide sequence having at least about 50%, at least about 60%, at least about 65%, at least about 70%, at least about 75%, at least about 80%, at least about 85%, at least about 90%, at least about 95%, at least about 97%, at least about 98%, at least about 99%, or more, nucleotide sequence identity with the sequence set forth in nucleotides 557–1618 of SEQ ID NO:01. In other embodiments, an insect ethanolamine kinase nucleic acid molecule comprises a nucleotide sequence having the sequence set forth in SEQ ID NO:01.

In some embodiments, an insect ethanolamine kinase nucleic acid molecule comprises a nucleotide sequence having at least about 50%, at least about 60%, at least about 65%, at least about 70%, at least about 75%, at least about 80%, at least about 85%, at least about 90%, at least about 95%, at least about 97%, at least about 98%, at least about 99%, or more, nucleotide sequence identity with the sequence set forth in nucleotides 536–1513 of SEQ ID NO:03. In other embodiments, an insect ethanolamine kinase nucleic acid molecule comprises a nucleotide sequence having the sequence set forth in SEQ ID NO:03.

In other embodiments, an insect ethanolamine kinase nucleic acid molecule comprises a fragment of at least about 18, at least about 25, at least about 30, at least about 35, at least about 40, at least about 50, at least about 75, at least about 100, at least about 125, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950, at least about 1000, or at least about 1060 contiguous nucleotides of nucleotides of the sequence set forth in nucleotides 557–1618 of SEQ ID NO:01.

In other embodiments, an insect ethanolamine kinase nucleic acid molecule comprises a fragment of at least about 18, at least about 25, at least about 30, at least about 35, at least about 40, at least about 50, at least about 75, at least about 100, at least about 125, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950, or at least about 970 contiguous nucleotides of nucleotides of the sequence set forth in nucleotides 536–1513 of SEQ ID NO:03.

In other embodiments, an insect ethanolamine kinase nucleic acid molecule comprises a nucleotide sequence encoding a polypeptide comprising an amino acid sequence having at least about 60%, at least about 65%, at least about 70%, at least about 75%, at least about 80%, at least about 85%, at least about 90%, or at least about 95%, amino acid sequence identity with the amino acid sequence set forth in SEQ ID NO:02. In some embodiments, an insect ethanolamine kinase nucleic acid molecule comprises a nucleotide sequence encoding a polypeptide comprising the sequence set forth in SEQ ID NO:02. In many of these embodiments, the encoded polypeptide has ethanolamine kinase activity.

In other embodiments, an insect ethanolamine kinase nucleic acid molecule comprises a nucleotide sequence encoding a polypeptide comprising an amino acid sequence having at least about 60%, at least about 65%, at least about 70%, at least about 75%, at least about 80%, at least about 85%, at least about 90%, or at least about 95%, amino acid sequence identity with the amino acid sequence set forth in SEQ ID NO:04. In some embodiments, an insect ethanolamine kinase nucleic acid molecule comprises a nucleotide sequence encoding a polypeptide comprising the sequence set forth in SEQ ID NO:04. In many of these embodiments, the encoded polypeptide has ethanolamine kinase activity.

In other embodiments, an insect ethanolamine kinase nucleic acid molecule comprises a nucleotide sequence encoding a polypeptide comprising a fragment of at least about 6, at least about 10, at least about 15, at least about 20, at least about 25, at least about 30, at least about 40, at least about 50, at least about 75, at least about 100, at least about 125, at least about 150, at least about 175, at least about 200, at least about 225, at least about 250, at least about 275, at least about 300, at least about 325, or at least about 350 contiguous amino acids of the sequence set forth in SEQ ID NO:02, up to the entire length of the amino acid sequence set forth in SEQ ID NO:02. In many of these embodiments, the encoded polypeptide has ethanolamine kinase activity.

In other embodiments, an insect ethanolamine kinase nucleic acid molecule comprises a nucleotide sequence encoding a polypeptide comprising a fragment of at least about 6, at least about 10, at least about 15, at least about 20, at least about 25, at least about 30, at least about 40, at least about 50, at least about 75, at least about 100, at least about 125, at least about 150, at least about 175, at least about 200, at least about 225, at least about 250, at least about 275, at least about 300, or at least about 325 contiguous amino acids of the sequence set forth in SEQ ID NO:04, up to the entire length of the amino acid sequence set forth in SEQ ID NO:04. In many of these embodiments, the encoded polypeptide has ethanolamine kinase activity.

Fragments of the subject nucleic acid molecules can be used for a variety of purposes. Interfering RNA (RNAi) fragments, particularly double-stranded (ds) RNAi, can be used to generate loss-of-function phenotypes, or to formulate biopesticides (discussed further below). The subject nucleic acid fragments are also useful as nucleic acid hybridization probes and replication/amplification primers. Certain "antisense" fragments, i.e. that are reverse complements of portions of the coding sequence of SEQ ID NO:01 or SEQ ID NO:03 have utility in inhibiting the function of a subject protein. The fragments are of length sufficient to specifically hybridize with a nucleic acid molecule having the sequence set forth in SEQ ID NO:01 or SEQ ID NO:03. The fragments consist of or comprise at least 12, at least 24, at least 36, or at least 96 contiguous nucleotides of SEQ ID NO:01 or SEQ ID NO:03. When the fragments are flanked by other nucleic acid sequences, the total length of the combined nucleic acid sequence is less than 15 kb, less than 10 kb, less than 5 kb, or less than 2 kb.

The subject nucleic acid sequences may consist solely of SEQ ID NO:01, SEQ ID NO:03, the open reading frame of SEQ ID NO:01, the open reading frame of SEQ ID NO:03 or fragments thereof. Alternatively, the subject nucleic acid sequences and fragments thereof may be joined to other components such as labels, peptides, agents that facilitate transport across cell membranes, hybridization-triggered cleavage agents or intercalating agents. The subject nucleic acid sequences and fragments thereof may also be joined to other nucleic acid sequences (i.e. they may comprise part of larger sequences) and are of synthetic/non-natural sequences and/or are isolated and/or are purified, i.e. unaccompanied by at least some of the material with which it is associated in its natural state. Generally, the isolated nucleic acids constitute at least about 0.5%, or at least about 5% by weight of the total nucleic acid present in a given fraction, and are often recombinant, meaning that they comprise a non-natural sequence or a natural sequence joined to nucleotide(s) other than that which it is joined to on a natural chromosome.

Derivative nucleic acid molecules of the subject nucleic acid molecules include sequences that hybridize to the nucleic acid sequence of SEQ ID NO:01 or SEQ ID NO:03, or to a nucleic acid molecule containing the open reading frame of SEQ ID NO:01 or SEQ ID NO:03, under stringency conditions such that the hybridizing derivative nucleic acid is related to the subject nucleic acid by a certain degree of sequence identity. A nucleic acid molecule is "hybridizable" to another nucleic acid molecule, such as a cDNA, genomic DNA, or RNA, when a single stranded form of the nucleic acid molecule can anneal to the other nucleic acid molecule. Stringency of hybridization refers to conditions under which nucleic acids are hybridizable. The degree of stringency can be controlled by temperature, ionic strength, pH, and the presence of denaturing agents such as formamide during hybridization and washing. As used herein, the term "stringent hybridization conditions" are those normally used by one of skill in the art to establish at least a 90% sequence identity between complementary pieces of DNA or DNA and RNA. "Moderately stringent hybridization conditions" are used to find derivatives having at least 70% sequence identity. Finally, "low-stringency hybridization conditions" are used to isolate derivative nucleic acid molecules that share at least about 50% sequence identity with the subject nucleic acid sequence.

The ultimate hybridization stringency reflects both the actual hybridization conditions as well as the washing conditions following the hybridization, and it is well known in the art how to vary the conditions to obtain the desired result. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing a nucleotide sequence as set forth in SEQ ID NO:01 or :03 (or the open reading frame thereof) under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5× Denhardt's solution, 0.05% sodium pyrophosphate and 100 µg/ml herring sperm DNA; hybridization for 18–20 hours at 65° C. in a solution containing 6×SSC, 1× Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate).

Derivative nucleic acid sequences that have at least about 70% sequence identity with SEQ ID NO:01 or SEQ ID NO:03 are capable of hybridizing to a nucleic acid molecule containing a nucleotide sequence as set forth in SEQ ID NO: 1 or :03 under moderately stringent conditions that comprise: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18–20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Other exemplary derivative nucleic acid sequences are capable of hybridizing to SEQ ID NO:01 under low stringency conditions that comprise: incubation for 8 hours to overnight at 37° C. in a solution comprising 20% formamide, 5×SSC, 50 mM sodium phosphate (pH 7.6), 5× Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As used herein, "percent (%) nucleic acid sequence identity" with respect to a subject sequence, or a specified portion of a subject sequence, is defined as the percentage of nucleotides in the candidate derivative nucleic acid sequence identical with the nucleotides in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410; http://blast.wustl.edu/blast/README.html; hereinafter referred to generally as "BLAST") with all the search parameters set to default values. The HSP S and HSP S2 parameters are dynamic values and are established by the program itself depending upon the composition of the particular sequence and composition of the particular database against which the sequence of interest is being searched. A percent (%) nucleic acid sequence identity value is determined by the number of matching identical nucleotides divided by the sequence length for which the percent identity is being reported.

In one exemplary embodiment, the derivative nucleic acid encodes a polypeptide comprising an amino acid sequence set forth in SEQ ID NO:02 or :04, or a fragment or derivative thereof as described further below. A derivative of a subject nucleic acid molecule, or fragment thereof, may comprise 100% sequence identity with SEQ ID NO:01 or :03 (or the open reading frame thereof), but may be a derivative thereof in the sense that it has one or more modifications at the base or sugar moiety, or phosphate backbone. Examples of modifications are well known in the art (Bailey, Ullmann's Encyclopedia of Industrial Chemistry (1998), 6th ed. Wiley and Sons). Such derivatives may be used to provide modified stability or any other desired property.

As used herein, a "derivative" nucleic acid or amino acid sequence includes orthologous sequences of SEQ ID NO:01, SEQ ID NO:02, SEQ ID NO:03, and SEQ ID NO:04, that are derived from other species. In some embodiments, the orthologue is from a heliothine species, for example *Heliocoverpa armigera* and *Heliothis zea*, which, together with *Heliothis virescens* are three of the world's major crop pests. Orthologous genes of these three species are extremely similar (The International Meeting on Genomics of Lepidoptera, Lyon, France Aug. 16–17, 2001; "International Lepidopteran Genome Project Proposal," Rev. Sep. 10, 2001; available at world wide web site ab.a.u-tokyo.acjp/lep-genome/.

In another example, it may be desired to develop a pesticidal agent that specifically targets a non-Heliothine insect species. In such case, it may be most efficient to develop biochemical screening assays (i.e., assays designed to identify molecules that can inhibit the protein target, as described hereinbelow) using the orthologous protein from that insect. While the orthologues in two species may have essentially the same function, differences in their protein structure may affect properties such as interactions with other proteins, compound binding and stability. Thus, results of a biochemical assays are most meaningful for the specific protein used in the assay. As used herein, orthologues include nucleic acid and polypeptide sequences.

Methods of identifying the orthologues in other species are known in the art. Normally, orthologues in different species retain the same function, due to presence of one or more protein motifs and/or 3-dimensional structures. In evolution, when a gene duplication event follows speciation, a single gene in one species, such as *Heliothis*, may correspond to multiple genes (paralogs) in another. As used herein, the term "orthologues" encompasses paralogs. When sequence data are available for a particular species, orthologues are generally identified by sequence homology analysis, such as BLAST analysis, usually using protein bait sequences. Sequences are assigned as a potential orthologue if the best hit sequence from the forward BLAST result retrieves the original query sequence in the reverse BLAST (Huynen MA and Bork P, Proc Natl Acad Sci (1998) 95:5849–5856; Huynen MA et al., Genome Research (2000) 10:1204–1210). Programs for multiple sequence alignment, such as CLUSTAL-W (Thompson JD et al, 1994, Nucleic Acids Res 22:4673–4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species.

Structural threading or other analysis of protein folding (e.g., using software by ProCeryon, Biosciences, Salzburg, Austria) may also identify potential orthologues. Nucleic acid hybridization methods may also be used to find orthologous genes, e.g., when sequence data are not available. Degenerate PCR and screening of cDNA or genomic DNA libraries are common methods for finding related gene sequences and are well known in the art (see, e.g., Sambrook et al. Molecular Cloning: A Laboratory Manual (Second Edition), Cold Spring Harbor Press, Plainview, N.Y., 1989; Dieffenbach C and Dveksler G (Eds.) PCR Primer: A Laboratory Manual, Cold Spring Harbor Laboratory Press, NY, 1989). For instance, methods for generating a cDNA library from an insect species of interest and probing the library with partially homologous gene probes are described in Sambrook et al. A highly conserved portion of the *Heliothis* ethanolamine kinase coding sequence may be used as a probe. Ethanolamine kinase orthologue nucleic acids may hybridize to the nucleic acid of SEQ ID NO:1 or SEQ ID NO:03 under high, moderate, or low stringency conditions.

After amplification or isolation of a segment of a putative orthologue, that segment may be cloned and sequenced by standard techniques and utilized as a probe to isolate a complete cDNA or genomic clone. Alternatively, it is possible to initiate an EST project to generate a database of sequence information for the species of interest. In another approach, antibodies that specifically bind known ethanolamine kinase polypeptides are used for orthologue isolation (Harlow E and Lane D, Antibodies: A Laboratory Manual, Cold Spring Harbor Laboratory Press, 1988, New York; Harlow E and Lane D, Using Antibodies: A Laboratory Manual, Cold Spring Harbor Laboratory Press, 1999, New York).

Western blot analysis can determine that a ethanolamine kinase orthologue (i.e., an orthologous protein) is present in a crude extract of tissue from a particular species. When reactivity is observed, the sequence encoding the candidate orthologue may be isolated by screening expression libraries representing the particular species. Expression libraries can be constructed in a variety of commercially available vectors, including lambda gt11, as described in Sambrook, et al. Once the candidate orthologue(s) are identified by any of these means, candidate orthologous sequence are used as bait (the "query") for the reverse BLAST against sequences from *Heliothis* or other species in which ethanolamine kinase nucleic acid and/or polypeptide sequences have been identified.

Another type of derivative of the subject nucleic acid sequences includes corresponding humanized sequences. A humanized nucleic acid sequence is one in which one or more codons have been substituted with a codon that is more commonly used in human genes. Preferably, a sufficient number of codons have been substituted such that a higher level of expression is achieved in mammalian cells than what would otherwise be achieved without the substitutions. Tables are available in the art that show, for each amino acid, the calculated codon frequency in humans genes for 1000 codons (Wada et al., Nucleic Acids Research (1990) 18(Suppl.):2367–2411). Similarly, other nucleic acid derivatives can be generated with codon usage optimized for expression in other organisms, such as yeasts, bacteria, and plants, where it is desired to engineer the expression of receptor proteins by using specific codons chosen according to the preferred codons used in highly expressed genes in each organism. Thus, a subject nucleic acid molecule in which the glutamic acid codon, GAA has been replaced with the codon GAG, which is more commonly used in human genes, is an example of a humanized nucleic acid molecule. A detailed discussion of the humanization of nucleic acid sequences is provided in U.S. Pat. No. 5,874,304 to Zolotukhin et al.

Isolation, Production, and Expression of Subject Nucleic Acid Molecules

The subject nucleic acid molecules, or fragments or derivatives thereof, may be obtained from an appropriate cDNA library prepared from any suitable insect species (including, but not limited to, *Drosophila*. and *Heliothis*). In many embodiments, a lepidopteran species is used, e.g., a heliothine species. Where the subject nucleic acid molecule is isolated from a Heliothine species, any of a variety of field and laboratory strains of various *Heliothis* species can be used, including, but not limited to, *Heliothis virescens, Heliothis maritima, Heliothis ononis, Heliothis peltigera, Heliothis phloxiphaga, Helicoverpa punctigera, Heliothis subflexa, Helicoverpa armigera*, and *Helicoverpa zea*.

An expression library can be constructed using known methods. For example, mRNA can be isolated to make cDNA which is ligated into a suitable expression vector for expression in a host cell into which it is introduced. Various screening assays can then be used to select for the gene or gene product (e.g. oligonucleotides of at least about 20 to 80 bases designed to identify the gene of interest, or labeled antibodies that specifically bind to the gene product). The gene and/or gene product can then be recovered from the host cell using known techniques.

A polymerase chain reaction (PCR) can also be used to isolate a subject nucleic acid molecule, where oligonucleotide primers representing fragmentary sequences of interest amplify RNA or DNA sequences from a source such as a genomic or cDNA library (as described by Sambrook et al., supra). Additionally, degenerate primers for amplifying homologs from any species of interest may be used. Once a PCR product of appropriate size and sequence is obtained, it may be cloned and sequenced by standard techniques, and utilized as a probe to isolate a complete cDNA or genomic clone.

Fragmentary sequences of the subject nucleic acid molecules and derivatives thereof may be synthesized by known methods. For example, oligonucleotides may be synthesized using an automated DNA synthesizer available from commercial suppliers (e.g. Biosearch, Novato, Calif.; Perkin-Elmer Applied Biosystems, Foster City, Calif.). Antisense RNA sequences can be produced intracellularly by transcription from an exogenous sequence, e.g. from vectors that contain subject antisense nucleic acid sequences. Newly generated sequences may be identified and isolated using standard methods.

An isolated subject nucleic acid molecule can be inserted into any appropriate cloning vector, for example bacteriophages such as lambda derivatives, or plasmids such as pBR322, pUC plasmid derivatives and the Bluescript vector (Stratagene, San Diego, Calif.). Recombinant molecules can be introduced into host cells via transformation, transfection, infection, electroporation, etc., or into a transgenic animal such as a fly. The transformed cells can be cultured to generate large quantities of the subject nucleic acid. Suitable methods for isolating and producing the subject nucleic acid sequences are well known in the art (Sambrook et al., supra; DNA Cloning: A Practical Approach, Vol. 1, 2, 3, 4, (1995) Glover, ed., MRL Press, Ltd., Oxford, U.K.).

The nucleotide sequence encoding a subject protein or fragment or derivative thereof, can be inserted into any appropriate expression vector for the transcription and translation of the inserted protein-coding sequence. Alternatively, the necessary transcriptional and translational signals can be supplied by the native subject gene and/or its flanking regions. A variety of host-vector systems may be utilized to express the protein-coding sequence such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, DNA, plasmid DNA, or cosmid DNA. Expression of a subject protein may be controlled by a suitable promoter/enhancer element. In addition, a host cell strain may be selected which modulates the expression of the inserted sequences, or modifies and processes the gene product in the specific fashion desired. Exemplary host cells include *E. coli*, lepidopteran Sf-9 or S-21 cells, and *Drosophila* S2 cells.

To detect expression of a subject gene product, the expression vector can comprise a promoter operably linked to a subject nucleic acid molecule, one or more origins of replication, and, one or more selectable markers (e.g. thymidine kinase activity, resistance to antibiotics, etc.). Alternatively, recombinant expression vectors can be identified by assaying for the expression of a subject gene product based on the physical or functional properties of a subject protein in in vitro assay systems (e.g. immunoassays).

A subject protein, fragment, or derivative may be optionally expressed as a fusion, or chimeric protein product (i.e. it is joined via a peptide bond to a heterologous protein sequence of a different, i.e., non-ethanolamine kinase, protein). In one embodiment, the subject protein is expressed as a fusion protein with a "tag" that facilitates purification, such as glutathione-S-transferase or (His)$_6$. A chimeric product can be made by ligating the appropriate nucleic acid sequences encoding the desired amino acid sequences to each other in the proper coding frame using standard methods and expressing the chimeric product. A chimeric product may also be made by protein synthetic techniques, e.g. by use of a peptide synthesizer.

Once a recombinant vector that expresses a subject nucleic acid molecule is identified, the encoded subject polypeptide can be isolated and purified using standard methods (e.g. ion exchange, affinity, and gel exclusion chromatography; centrifugation; differential solubility; electrophoresis). The amino acid sequence of the protein can be deduced from the nucleotide sequence of the recombinant nucleic acid molecule contained in the recombinant vector and can thus be synthesized by standard chemical methods (Hunkapiller et al., Nature (1984) 310:105–111). Alternatively, native subject proteins can be purified from natural sources, by standard methods (e.g. immunoaffinity purification).

Recombinant Vectors and Host Cells

Also provided are constructs ("recombinant vectors") comprising the subject nucleic acids inserted into a vector, and host cells comprising the constructs. The subject constructs are used for a number of different applications, including propagation, protein production, etc. Viral and non-viral vectors may be prepared and used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal. The choice of appropriate vector is well within the skill of the art. Many such vectors are available commercially.

To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject proteins. For expression, the gene product encoded by a polynucleotide of the invention is expressed in any convenient expression system, including, for example, bacterial, yeast, insect, amphibian, and mammalian systems. Suitable vectors and host cells are described in U.S. Pat. No. 5,654,173. In the expression vector, an ethanolamine kinase-encoding polynucleotide, e.g., as set forth in SEQ ID NO: 01 or :03, is operably linked to a regulatory sequence as appropriate to obtain the desired expression properties. These can include promoters (attached either at the 5' end of the sense strand or at the 3' end of the antisense strand), enhancers, terminators, operators, repressors, and inducers. The promoters can be regulated or constitutive. In some situations it may be desirable to use conditionally active promoters, such as tissue-specific, or developmental stage-specific promoters. These are linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject ethanolamine kinase gene, or may be derived from exogenous sources.

Expression vectors generally have convenient restriction sites located near the promoter sequence to provide for the insertion of nucleic acid sequences encoding heterologous proteins. A selectable marker operative in the expression host may be present, for detection of host cells that comprise the recombinant vector. A variety of markers are known and may be present on the vector, where such markers include those that confer antibiotic resistance, e.g. resistance to ampicillin, tetracycline, chloramphenicol, kanamycin, neomycin; markers that provide for histochemical detection, etc. Expression vectors may be used for, among other things, the production of subject proteins, subject fusion proteins, as described above, and for use in screening assays, as described below.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, or for use in screening assays as described herein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, *Xenopus oocytes*, lepidopteran Sf-9 or S-21 cells, *Drosophila* S2 cells, may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979) 281:544; Goeddel et al., *Nucleic Acids Res*. (1980) 8:4057; EP 0 036,776; U.S. Pat. No. 4,551,433; DeBoer et al, *Proc. Natl. Acad. Sci. (USA)* (1983) 80:21–25; and Siebenlist et al., *Cell* (1980) 20:269.

Yeast. Expression systems in yeast include those described in Hinnen et al., *Proc. Natl. Acad. Sci. (USA)* (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154:737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284–289; Tilburn et al., *Gene* (1983) 26:205–221; Yelton et al., *Proc. Natl. Acad. Sci. (USA)* (1984) 81:1470–1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765–776; Miller et al., *Ann. Rev. Microbiol.* (1988) 42:177; Carbonell et al., *Gene* (1988) 73:409; Maeda et al., *Nature* (1985) 315:592–594; Lebacq-Verheyden et al., *Mol. Cell. Biol.* (1988) 8:3129; Smith et al., *Proc. Natl. Acad. Sci. (USA)* (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594. Various insect cells, including lepidopteran Sf-9 cells and S-21 cells, and *Drosophila* S2 cells, have been amply described in the art. See, e.g., "Insect Cell Culture Engineering", Goosen, Daugulis, and Faulkner, eds. (1993) Marcel Dekker.

Mammalian Cells. Mammalian expression is accomplished as described in Dijkema et al., *EMBO J.* (1985) 4:761, Gorman et al., *Proc. Natl. Acad. Sci. (USA)* (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. RE No. 30,985.

Plant cells. Plant cell culture is amply described in various publications, including, e.g., *Plant Cell Culture: A Practical Approach*, (1995) R. A. Dixon and R. A. Gonzales, eds., IRL Press; and U.S. Pat. No. 6,069,009.

Following preparation of the expression vector, the expression vector will be introduced into an appropriate host cell for production of the subject polypeptide, i.e. a host cell will be transformed with the expression vector. Introduction of the recombinant vector into a host cell is accomplished in any convenient manner, including, but not limited to, calcium phosphate precipitation, electroporation, microinjection, use of lipids (e.g., lipofectin), infection, and the like.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

The invention further provides recombinant host cells, as described above, which contain a subject recombinant vector comprising a subject ethanolamine kinase nucleic acid molecule, e.g., as part of a recombinant vector, either extrachromosomally or integrated into the genome of the host cell. Recombinant host cells are generally isolated, but may also be part of a multicellular organism, e.g., a transgenic animal. Thus, the invention further provides transgenic, non-human animals, particularly insects, that comprise a subject ethanolamine kinase nucleic acid molecule.

The subject nucleic acid molecules can be used to generate transgenic, non-human animals or plants, or site-specific gene modifications in cell lines. Transgenic animals and plants may be made through homologous recombination, where the endogenous locus is altered. Alternatively, a nucleic acid construct is randomly integrated into the genome. Vectors for stable integration include plasmids, retroviruses and other animal viruses, YACs, and the like. Transgenic insects are useful in screening assays, as described below. Insect transgenesis has been described in, e.g., "Insect Transgenesis: Methods and Applications" Handler and James, eds. (2000) CRC Press.

Isolated Polypeptides of the Invention

The invention further provides isolated polypeptides comprising or consisting of an amino acid sequence of SEQ ID NO:02, SEQ ID NO:04, or fragments, variants, or derivatives (e.g., orthologues) thereof. Compositions comprising any of these proteins may consist essentially of a subject protein, fragments, or derivatives, or may comprise additional components (e.g. pharmaceutically acceptable carriers or excipients, culture media, carriers used in pesticide formulations, etc.).

A derivative of a subject protein typically shares a certain degree of sequence identity or sequence similarity with SEQ ID NO:02 or SEQ ID NO:04, or a fragment thereof. As used herein, "percent (%) amino acid sequence identity" with respect to a subject sequence, or a specified portion of a subject sequence, is defined as the percentage of amino acids in the candidate derivative amino acid sequence identical with the amino acid in the subject sequence (or specified portion thereof), after aligning the sequences and introducing gaps, if necessary to achieve the maximum percent sequence identity, as generated by BLAST (Altschul et al., supra) using the same parameters discussed above for derivative nucleic acid sequences. A % amino acid sequence identity value is determined by the number of matching identical amino acids divided by the sequence length for which the percent identity is being reported.

"Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine, and glycine.

In some embodiments, a subject protein variant or derivative shares at least about 60%, at least about 65%, at least about 70%, at least about 75%, at least 80% sequence identity or similarity, at least 85%, at least 90%, at least about 95%, at least about 97%, at least about 98%, or at least about 99% sequence identity or similarity with a contiguous stretch of at least 25 amino acids, at least 50 amino acids, at least 100 amino acids, at least 200 amino acids, at least 300 amino acids, or at least 350 amino acids, and in some cases, the entire length of SEQ ID NO:02. In some embodiments, a polypeptide of the invention comprises an amino acid sequence as set forth in SEQ ID NO:02.

In some embodiments, a subject protein variant or derivative shares at least about 60%, at least about 65%, at least about 70%, at least about 75%, at least 80% sequence identity or similarity, at least 85%, at least 90%, at least about 95%, at least about 97%, at least about 98%, or at least about 99% sequence identity or similarity with a contiguous stretch of at least 25 amino acids, preferably at least 50 amino acids, more preferably at least 100 amino acids, at least 200 amino acids, at least 300 amino acids, or at least 325 amino acids, and in some cases, the entire length of SEQ ID NO:04. In some embodiments, a polypeptide of the invention comprises an amino acid sequence as set forth in SEQ ID NO:04.

In some embodiments, an ethanolamine kinase polypeptide of the invention comprises a fragment of at least about 6, at least about 10, at least about 15, at least about 20, at least about 25, at least about 30, at least about 40, at least about 50, at least about 75, at least about 100, at least about 125, at least about 150, at least about 175, at least about 200, at least about 225, at least about 250, at least about 275, at least about 300, at least about 325, or at least about 350 contiguous amino acids of the sequence set forth in SEQ ID NO:02, up to the entire sequence set forth in SEQ ID NO:02. In many of these embodiments, the ethanolamine kinase polypeptide has ethanolamine kinase enzyme activity.

In some embodiments, an ethanolamine kinase polypeptide of the invention comprises a fragment of at least about 6, at least about 10, at least about 15, at least about 20, at least about 25, at least about 30, at least about 40, at least about 50, at least about 75, at least about 100, at least about 125, at least about 150, at least about 175, at least about 200, at least about 225, at least about 250, at least about 275, at least about 300, or at least about 325 contiguous amino acids of the sequence set forth in SEQ ID NO:04, up to the entire sequence set forth in SEQ ID NO:04. In many of these embodiments, the ethanolamine kinase polypeptide has ethanolamine kinase enzyme activity.

The fragment or derivative of a subject protein is preferably "functionally active" meaning that the subject protein derivative or fragment exhibits one or more functional activities associated with a full-length, wild-type subject protein comprising the amino acid sequence of SEQ ID NO:02 or SEQ ID NO:04. As one example, a fragment or derivative may have antigenicity such that it can be used in immunoassays, for immunization, for inhibition of activity of a subject protein, etc, as discussed further below regarding generation of antibodies to subject proteins. In many embodiments, a functionally active fragment or derivative of a subject protein is one that displays one or more biological activities associated with a subject protein, such as catalytic activity. For purposes herein, functionally active fragments also include those fragments that exhibit one or more structural features of a subject protein, such as transmembrane or enzymatic domains. Protein domains can be identified using the PFAM program (see, e.g., Bateman A., et al., Nucleic Acids Res, 1999, 27:260–2; and the world wide web at pfam.wustle.edu.

The functional activity of the subject proteins, derivatives and fragments can be assayed by various methods known to one skilled in the art (Current Protocols in Protein Science (1998) Coligan et al., eds., John Wiley & Sons, Inc., Somerset, N.J.). Enzymatic activity of a subject ethanolamine kinase is assayed by measuring the oxidation of NADH at 340 nm. The kinase reaction product ADP is assayed in a continuous manner using pyruvate kinase, lactate dehydrogenase and the substrates physphoenoylpyruvate (PEP), NADH, and ADP. Pyruvate kinase forms pyruvate from PEP, with concomitant phosphoryl transfer from PEP to ADP to give ATP. The pyruvate that is formed is then reduced by lactate dehydrogenase to lactate, with concomitant oxidation of NADH to $NAD^+$ and $H^+$. The decrease in absorbance at 340 nm is measured when NADH is oxidized.

A non-limiting example of an assay for ethanolamine kinase activity is provided in Example 2. In the assay described in Example 2, depletion of ATP that follows the phosphorylation of ethanolamine by ATP is measured. Remaining ATP is measured biochemically by luciferase, which consumes ATP and emits light. The quantity of light emitted is proportional to the concentration of ATP remaining in the reaction mixture.

The subject proteins and polypeptides may be obtained from naturally occurring sources or synthetically produced. For example, wild type proteins may be derived from biological sources which express the proteins, e.g., *Heliothis*. The subject proteins may also be derived from synthetic means, e.g. by expressing a recombinant gene encoding protein of interest in a suitable host, as described above. Any convenient protein purification procedures may be employed, where suitable protein purification methodologies are described in Guide to Protein Purification, (Deuthser ed.) (Academic Press, 1990). For example, a lysate may prepared from the original source and purified using HPLC, exclusion chromatography, gel electrophoresis, affinity chromatography, and the like.

A derivative of a subject protein can be produced by various methods known in the art. The manipulations which result in their production can occur at the gene or protein level. For example, a cloned subject gene sequence can be cleaved at appropriate sites with restriction endonuclease(s) (Wells et al., Philos. Trans. R. Soc. London SerA (1986) 317:415), followed by further enzymatic modification if desired, isolated, and ligated in vitro, and expressed to produce the desired derivative. Alternatively, a subject gene can be mutated in vitro or in vivo, to create and/or destroy translation, initiation, and/or termination sequences, or to create variations in coding regions and/or to form new restriction endonuclease sites or destroy preexisting ones, to facilitate further in vitro modification. A variety of mutagenesis techniques are known in the art such as chemical mutagenesis, in vitro site-directed mutagenesis (Carter et al., Nucl. Acids Res. (1986) 13:4331), use of TAB® linkers (available from Pharmacia and Upjohn, Kalamazoo, Mich.), etc.

At the protein level, manipulations include post translational modification, e.g. glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known technique (e.g. specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.). Derivative proteins can also be chemically synthesized by use of a peptide synthesizer, for example to introduce nonclassical amino acids or chemical amino acid analogs as substitutions or additions into the subject protein sequence.

Chimeric or fusion proteins can be made comprising a subject protein or fragment thereof (preferably comprising one or more structural or functional domains of the subject protein) joined at its amino- or carboxy-terminus via a peptide bond to an amino acid sequence of a different protein. Chimeric proteins can be produced by any known method, including: recombinant expression of a nucleic acid encoding the protein (comprising an amino acid sequence encoding a subject protein joined in-frame to a coding sequence for a different protein); ligating the appropriate nucleic acid sequences encoding the desired amino acid sequences to each other in the proper coding frame, and expressing the chimeric product; and protein synthetic techniques, e.g. by use of a peptide synthesizer.

Gene Regulatory Elements of the Subject Nucleic Acid Molecules

The invention further provides gene regulatory DNA elements, such as enhancers or promoters that control transcription of the subject nucleic acid molecules. Such regulatory elements can be used to identify tissues, cells, genes and factors that specifically control production of a subject protein. Analyzing components that are specific to a particular subject protein function can lead to an understanding of how to manipulate these regulatory processes, especially for pesticide and therapeutic applications, as well as an understanding of how to diagnose dysfunction in these processes.

Gene fusions with the subject regulatory elements can be made. For compact genes that have relatively few and small intervening sequences, such as those described herein for *Heliothis*, it is typically the case that the regulatory elements that control spatial and temporal expression patterns are found in the DNA immediately upstream of the coding region, extending to the nearest neighboring gene. Regulatory regions can be used to construct gene fusions where the regulatory DNAs are operably fused to a coding region for a reporter protein whose expression is easily detected, and these constructs are introduced as transgenes into the animal of choice.

An entire regulatory DNA region can be used, or the regulatory region can be divided into smaller segments to identify sub-elements that might be specific for controlling expression a given cell type or stage of development. Reporter proteins that can be used for construction of these gene fusions include *E. coli* beta-galactosidase and green fluorescent protein (GFP). These can be detected readily in situ, and thus are useful for histological studies and can be used to sort cells that express a subject protein (O'Kane and Gehring PNAS (1987) 84(24):9123–9127; Chalfie et al., Science (1994) 263:802–805; and Cumberledge and Krasnow (1994) Methods in Cell Biology 44:143–159). Recombinase proteins, such as FLP or cre, can be used in controlling gene expression through site-specific recombination (Golic and Lindquist (1989) Cell 59(3):499–509; White et al., Science (1996) 271:805–807). Toxic proteins such as the reaper and hid cell death proteins, are useful to specifically ablate cells that normally express a subject protein in order to assess the physiological function of the cells (Kingston, In Current Protocols in Molecular Biology (1998) Ausubel et al., John Wiley & Sons, Inc. sections 12.0.3–12.10) or any other protein where it is desired to examine the function this particular protein specifically in cells that synthesize a subject protein.

Alternatively, a binary reporter system can be used, similar to that described further below, where a subject regulatory element is operably fused to the coding region of an exogenous transcriptional activator protein, such as the GAL4 or tTA activators described below, to create a subject regulatory element "driver gene". For the other half of the binary system the exogenous activator controls a separate "target gene" containing a coding region of a reporter protein operably fused to a cognate regulatory element for the exogenous activator protein, such as $UAS_G$ or a tTA-response element, respectively. An advantage of a binary system is that a single driver gene construct can be used to activate transcription from preconstructed target genes encoding different reporter proteins, each with its own uses as delineated above.

Subject regulatory element-reporter gene fusions are also useful for tests of genetic interactions, where the objective is to identify those genes that have a specific role in controlling the expression of subject genes, or promoting the growth and differentiation of the tissues that expresses a subject protein. Subject gene regulatory DNA elements are also useful in protein-DNA binding assays to identify gene regulatory proteins that control the expression of subject genes. The gene regulatory proteins can be detected using a variety of methods that probe specific protein-DNA interactions well known to those skilled in the art (Kingston, supra) including in vivo footprinting assays based on protection of DNA sequences from chemical and enzymatic modification within living or permeabilized cells; and in vitro footprinting assays based on protection of DNA sequences from chemical or enzymatic modification using protein extracts, nitrocellulose filter-binding assays and gel electrophoresis mobility shift assays using radioactively labeled regulatory DNA elements mixed with protein extracts. Candidate gene regulatory proteins can be purified using a combination of conventional and DNA-affinity purification techniques. Molecular cloning strategies can also be used to identify proteins that specifically bind subject gene regulatory DNA elements. For example, a *Drosophila* cDNA library in an expression vector, can be screened for cDNAs that encode subject gene regulatory element DNA-binding activity. Similarly, the yeast "one-hybrid" system can be used (Li and Herskowitz, Science (1993) 262:1870–1874; Luo et al., *Biotechniques* (1996) 20(4):564–568; Vidal et al., *Proc. Natl. Acad. Sci. USA* (1996) 93(19):10315–10320).

Antibodies Specific for Subject Proteins

The present invention provides antibodies, which may be isolated antibodies, which bind specifically to a subject protein. The subject proteins, fragments thereof, and derivatives thereof may be used as an immunogen to generate monoclonal or polyclonal antibodies and antibody fragments or derivatives (e.g. chimeric, single chain, Fab fragments). As used herein, the term "antibodies" includes antibodies of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. Also provided are "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516,637; 5,223,409; 5,658,727; 5,667,988; 5,498, 538; 5,403,484; 5,571,698; and 5,625,033.

The antibodies may be detectably labeled, e.g., with a radioisotope, an enzyme which generates a detectable product, a green fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. For example, fragments of a subject protein, e.g., those identified as hydrophilic, are used as immunogens for antibody production using art-known methods such as by hybridomas; production of monoclonal antibodies in germ-free animals (PCT/US90/02545); the use of human hybridomas (Cole et al., *Proc. Natl. Acad. Sci. USA* (1983) 80:2026–2030; Cole et al., in Monoclonal Antibodies and Cancer Therapy (1985) Alan R. Liss, pp. 77–96), and production of humanized antibodies (Jones et al., Nature (1986) 321:522–525; U.S. Pat. No. 5,530,101). In a particular embodiment, subject polypeptide fragments provide specific antigens and/or immunogens, especially when coupled to carrier proteins. For example, peptides are covalently coupled to keyhole limpet antigen (KLH) and the conjugate is emulsified in Freund's complete adjuvant. Laboratory animals, e.g., mice, rats, or rabbits are immunized according to conventional protocol and bled. The presence of specific antibodies is assayed by solid phase immunosorbent assays using immobilized corresponding polypeptide. Specific activity or function of the antibodies produced may be determined by convenient in vitro, cell-based, or in vivo assays: e.g. in vitro binding assays, etc. Binding affinity may be assayed by determination of equilibrium constants of antigen-antibody association (usually at least about $10^7 M^{-1}$, at least about $10^8 M^{-1}$, or at least about $10^9 M^{-1}$).

Screening Methods

The present invention further provides methods of identifying agents that reduce an enzymatic activity of a subject ethanolamine kinase, that reduce the level of ethanolamine kinase mRNA and/or polypeptide levels in a cell, particularly an insect cell. The invention further provides methods for identifying molecules that interact with a subject ethanolamine kinase.

Methods for Identifying Molecules that Interact with a Subject Protein

A variety of methods can be used to identify or screen for molecules, such as proteins or other molecules, that interact with a subject protein, or derivatives or fragments thereof. The assays may employ purified protein, or cell lines or model organisms such as *Heliothis, Drosophila,* and *C. elegans,* that have been genetically engineered to express a subject protein. Suitable screening methodologies are well known in the art to test for proteins and other molecules that interact with a subject gene and protein (see e.g., PCT International Publication No. WO 96/34099). The newly identified interacting molecules may provide new targets for pharmaceutical or pesticidal agents. Any of a variety of exogenous molecules, both naturally occurring and/or synthetic (e.g., libraries of small molecules or peptides, or phage display libraries), may be screened for binding capacity. In a typical binding experiment, a subject protein or fragment is mixed with candidate molecules under conditions conducive to binding, sufficient time is allowed for any binding to occur, and assays are performed to test for bound complexes.

Assays to find interacting proteins can be performed by any method known in the art, for example, immunoprecipitation with an antibody that binds to the protein in a complex followed by analysis by size fractionation of the immunoprecipitated proteins (e.g. by denaturing or nondenaturing polyacrylamide gel electrophoresis), Western analysis, non-denaturing gel electrophoresis, two-hybrid systems (Fields and Song, Nature (1989) 340:245–246; U.S. Pat. No. 5,283, 173; for review see Brent and Finley, Annu. Rev. Genet. (1977) 31:663–704), etc.

Immunoassays

Immunoassays can be used to identify proteins that interact with or bind to a subject protein. Various assays are available for testing the ability of a protein to bind to or compete with binding to a wild-type subject protein or for binding to an anti-subject protein antibody. Suitable assays include radioimmunoassays, ELISA (enzyme linked immunosorbent assay), immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, immunoelectrophoresis assays, etc.

One or more of the molecules in the immunoassay may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

Identification of Potential Pesticide or Drug Targets

The present invention further provides methods of identifying agents that reduce an enzymatic activity of a subject ethanolamine kinase, that reduce the level of ethanolamine kinase mRNA and/or polypeptide levels in a cell, particularly an insect cell.

Once new target genes or target interacting genes are identified, they can be assessed as potential pesticide or drug targets, or as potential biopesticides. Further, transgenic plants that express subject proteins can be tested for activity against insect pests (Estruch et al., Nat. Biotechnol (1997) 15(2):137–141).

The subject proteins are validated pesticide targets, since disruption in *Drosophila* of the subject genes results in lethality when homozygous. The mutation to lethality of these gene indicates that drugs that agonize or antagonize the gene product may be effective pesticidal agents.

As used herein, the term "pesticide" refers generally to chemicals, biological agents, and other compounds that adversely affect insect viability, e.g., that kill, paralyze, sterilize or otherwise disable pest species in the areas of agricultural crop protection, human and animal health. Exemplary pest species include parasites and disease vectors such as mosquitoes, fleas, ticks, parasitic nematodes, chiggers, mites, etc. Pest species also include those that are eradicated for aesthetic and hygienic purposes (e.g. ants, cockroaches, clothes moths, flour beetles, etc.), home and garden applications, and protection of structures (including wood boring pests such as termites, and marine surface fouling organisms).

Pesticidal compounds can include traditional small organic molecule pesticides (typified by compound classes such as the organophosphates, pyrethroids, carbamates, and organochlorines, benzoylureas, etc.). Other pesticides include proteinaceous toxins such as the *Bacillus thuringiensis* Crytoxins (Gill et al., Annu Rev Entomol (1992) 37:615–636) and *Photorabdus luminescens* toxins (Bowden et al., Science (1998) 280:2129–2132); and nucleic acids such as subject dsRNA or antisense nucleic acids that interfere with activity of a subject nucleic acid molecule.

The terms "candidate agent," "agent", "substance" and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents that reduce an ethanolamine kinase activity of a subject polypeptide, and/or that reduce a level of ethanolamine kinase mRNA and/or polypeptide by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more, are candidate pesticides.

Candidate agents that reduce enzymatic activity of a subject ethanolamine kinase and/or that reduce a level of ethanolamine kinase mRNA and/or polypeptide are further tested for toxicity toward vertebrate species, such as mammalian species, etc.; and for bioavailability.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components are added in any order that provides for the requisite activity. Incubations are performed at any suitable temperature, typically between 4EC and 40EC. Incubation periods are selected for optimum activity, but may also be optimized to facilitate rapid high-throughput screening. Typically between 0.1 and 1 hour will be sufficient.

Assays of Compounds on Purified Ethanolamine Kinase

The invention provides methods of screening for agents that modulate an enzymatic activity of a subject ethanolamine kinase. Such agents are useful as pesticidal agents. Ethanolamine kinase enzymatic activity is measured as described in the Examples, below. In general, enzymatic activity of a subject ethanolamine kinase is assayed by measuring the oxidation of NADH at 340 nm. The kinase reaction product ADP is assayed in a continuous manner using pyruvate kinase, lactate dehydrogenase and the substrates physphoenoylpyruvate (PEP), NADH, and ADP. Pyruvate kinase forms pyruvate from PEP, with concomitant phosphoryl transfer from PEP to ADP to give ATP. The pyruvate that is formed is then reduced by lactate dehydrogenase to lactate, with concomitant oxidation of NADH to $NAD^+$ and $H^+$. The decrease in absorbance at 340 nm is measured when NADH is oxidized.

The present invention provides methods of identifying agents which modulate an enzymatic activity of an ethanolamine kinase polypeptide of the invention. The term "modulate" encompasses an increase or a decrease in the measured ethanolamine kinase activity when compared to a suitable control.

The method generally comprises: a) contacting a test agent with a sample containing an ethanolamine kinase polypeptide; and b) assaying an ethanolamine kinase activity of the ethanolamine kinase polypeptide in the presence of the test agent. An increase or a decrease in ethanolamine kinase activity in comparison to ethanolamine kinase activity in a suitable control (e.g., a sample comprising an ethanolamine kinase polypeptide in the absence of the agent being tested) is an indication that the agent modulates an enzymatic activity of the ethanolamine kinase.

An "agent which modulates an ethanolamine kinase activity of an ethanolamine kinase polypeptide", as used herein, describes any molecule, e.g. synthetic or natural organic or inorganic compound, protein or pharmaceutical, with the capability of altering an ethanolamine kinase activity of an ethanolamine kinase polypeptide, as described herein. Generally a plurality of assay mixtures is run in parallel with different agent concentrations to obtain a differential response to the various concentrations. Typically, one of these concentrations serves as a negative control, i.e. at zero concentration or below the level of detection.

Assays of Compounds on Insects

Potential insecticidal compounds can be administered to insects in a variety of ways, including orally (including addition to synthetic diet, application to plants or prey to be consumed by the test organism), topically (including spraying, direct application of compound to animal, allowing animal to contact a treated surface), or by injection. Insecticides are typically very hydrophobic molecules and must commonly be dissolved in organic solvents, which are allowed to evaporate in the case of methanol or acetone, or at low concentrations can be included to facilitate uptake (ethanol, dimethyl sulfoxide).

The first step in an insect assay is usually the determination of the minimal lethal dose (MLD) on the insects after a chronic exposure to the compounds. The compounds are usually diluted in DMSO, and applied to the food surface bearing 0–48 hour old embryos and larvae. In addition to MLD, this step allows the determination of the fraction of eggs that hatch, behavior of the larvae, such as how they move/feed compared to untreated larvae, the fraction that survive to pupate, and the fraction that eclose (emergence of the adult insect from puparium). Based on these results more detailed assays with shorter exposure times may be designed, and larvae might be dissected to look for obvious morphological defects. Once the MLD is determined, more specific acute and chronic assays can be designed.

In a typical acute assay, compounds are applied to the food surface for embryos, larvae, or adults, and the animals are observed after 2 hours and after an overnight incubation. For application on embryos, defects in development and the percent that survive to adulthood are determined. For larvae, defects in behavior, locomotion, and molting may be observed. For application on adults, defects in levels and/or enzyme activity are observed, and effects on behavior and/or fertility are noted.

For a chronic exposure assay, adults are placed on vials containing the compounds for 48 hours, then transferred to a clean container and observed for fertility, defects in levels and/or activity of a subject enzyme, and death.

Assay of Compounds using Cell Cultures

Compounds that modulate (e.g. block or enhance) a subject protein's activity and/or that modulate a level of ethanolamine kinase mRNA or polypeptide may also be assayed using cell culture. Exemplary cells are cultured insect cells such as *Drosophila* S2 cells. In some embodiments, a recombinant vector that includes a sequence that encodes all or part of a subject ethanolamine kinase is introduced into cells in in vitro culture, and the resulting recombinant host cells are used to screen test agents. For example, various compounds added to cells expressing a subject protein may be screened for their ability to modulate the activity of subject genes based upon measurements of a biological activity of a subject protein. For example, compounds may be screened for their ability to modulate the activity of ethanolamine kinase genes based on measurements of ethanolamine kinase activity, ethanolamine kinase mRNA levels or ethanolamine kinase polypeptide levels.

Assays for changes in a biological activity of a subject protein can be performed on cultured cells expressing endogenous normal or mutant subject protein. Such studies also can be performed on cells transfected with vectors capable of expressing the subject protein, or functional domains of one of the subject protein, in normal or mutant form. In addition, to enhance the signal measured in such assays, cells may be cotransfected with nucleic acid molecules, or a subject recombinant vector, encoding a subject protein.

Alternatively, cells expressing a subject protein may be lysed, the subject protein purified, and tested in vitro using methods known in the art (Kanemaki M., et al., J Biol Chem, (1999) 274:22437–22444).

A wide variety of cell-based assays may be used for identifying agents which modulate levels of ethanolamine kinase mRNA, for identifying agents that modulate the level of ethanolamine kinase polypeptide, and for identifying agents that modulate the level of ethanolamine kinase activity in a eukaryotic cell, using, for example, an insect cell (e.g., *Drosophila* S2 cells) transformed with a construct comprising an ethanolamine kinase-encoding cDNA such that the cDNA is expressed, or, alternatively, a construct comprising an ethanolamine kinase promoter operably linked to a reporter gene.

Accordingly, the present invention provides a method for identifying an agent, particularly a biologically active agent, that modulates a level of ethanolamine kinase expression in a cell, the method comprising: combining a candidate agent to be tested with a cell comprising a nucleic acid which encodes an ethanolamine kinase polypeptide; and determining the effect of said agent on ethanolamine kinase expression (e.g., determining the effect of the agent on a level of ethanolamine kinase mRNA, a level of ethanolamine kinase polypeptide, or a level of ethanolamine kinase enzyme activity in the cell).

"Modulation" of ethanolamine kinase expression levels includes increasing the level and decreasing the level of ethanolamine kinase mRNA and/or ethanolamine kinase polypeptide encoded by the ethanolamine kinase polynucleotide and/or the level of ethanolamine kinase activity when compared to a control lacking the agent being tested. An increase or decrease of about 1.25-fold, usually at least about 1.5-fold, usually at least about 2-fold, usually at least about 5-fold, usually at least about 10-fold or more, in the level (i.e., an amount) of ethanolamine kinase mRNA and/or polypeptide and/or ethanolamine kinase enzyme activity following contacting the cell with a candidate agent being tested, compared to a control to which no agent is added, is an indication that the agent modulates ethanolamine kinase mRNA levels, ethanolamine kinase polypeptide levels, or ethanolamine kinase enzyme activity in the cell. Of particular interest in many embodiments are candidate agents that reduce a level of ethanolamine kinase mRNA, and/or reduce a level of ethanolamine kinase polypeptide, and/or reduce a level of ethanolamine kinase enzyme activity in an insect cell.

ethanolamine kinase mRNA and/or polypeptide whose levels or activity are being measured can be encoded by an endogenous ethanolamine kinase polynucleotide, or the ethanolamine kinase polynucleotide can be one that is comprised within a recombinant vector and introduced into the cell, i.e., the ethanolamine kinase mRNA and/or polypeptide can be encoded by an exogenous ethanolamine kinase polynucleotide. For example, a recombinant vector may comprise an isolated ethanolamine kinase transcriptional regulatory sequence, such as a promoter sequence, operably linked to a reporter gene (e.g,. β-galactosidase, CAT, luciferase, or other gene whose product can be easily assayed). In these embodiments, the method for identifying an agent that modulates a level of ethanolamine kinase expression in a cell, comprises: combining a candidate agent to be tested with a cell comprising a nucleic acid which comprises an ethanolamine kinase gene transcriptional regulatory element operably linked to a reporter gene; and determining the effect of said agent on reporter gene expression.

A recombinant vector may comprise an isolated ethanolamine kinase transcriptional regulatory sequence, such as a promoter sequence, operably linked to sequences coding for an ethanolamine kinase polypeptide; or the transcriptional control sequences can be operably linked to coding sequences for an ethanolamine kinase fusion protein comprising ethanolamine kinase polypeptide fused to a polypeptide which facilitates detection. In these embodiments, the method comprises combining a candidate agent to be tested with a cell comprising a nucleic acid which comprises an ethanolamine kinase gene transcriptional regulatory element operably linked to an ethanolamine kinase polypeptide-coding sequence; and determining the effect of said agent on ethanolamine kinase expression, which determination can be carried out by measuring an amount of ethanolamine kinase mRNA, ethanolamine kinase polypeptide, ethanolamine kinase fusion polypeptide, or ethanolamine kinase enzyme activity produced by the cell.

Cell-based assays generally comprise the steps of contacting the cell with an agent to be tested, forming a test sample, and, after a suitable time, assessing the effect of the agent on ethanol amine kinase mRNA levels, ethanol amine kinase polypeptide and/or enzyme levels. A control sample comprises the same cell without the candidate agent added. ethanolamine kinase expression levels are measured in both the test sample and the control sample. A comparison is made between ethanolamine kinase expression level in the test sample and the control sample. ethanolamine kinase expression can be assessed using conventional assays. For example, when a cell line is transformed with a construct that results in expression of ethanolamine kinase, ethanolamine kinase mRNA levels can be detected and measured, or ethanolamine kinase polypeptide levels, and/or ethanolamine kinase enzyme levels can be detected and measured. A suitable period of time for contacting the agent with the cell can be determined empirically, and is generally a time sufficient to allow entry of the agent into the cell and to allow the agent to have a measurable effect on ethanolamine kinase mRNA and/or polypeptide levels and/or enzyme activity. Generally, a suitable time is between 10 minutes and 24 hours, more typically about 1–8 hours.

Methods of measuring ethanolamine kinase mRNA levels are known in the art, several of which have been described above, and any of these methods can be used in the methods of the present invention to identify an agent which modulates ethanolamine kinase mRNA level in a cell, including, but not limited to, a PCR, such as a PCR employing detectably labeled oligonucleotide primers, and any of a variety of hybridization assays. Similarly, ethanolamine kinase polypeptide levels can be measured using any standard method, several of which have been described herein, including, but not limited to, an immunoassay such as ELISA, for example an ELISA employing a detectably labeled antibody specific for an ethanolamine kinase polypeptide. Ethanolamine kinase enzyme activity can be measured as described above.

Compounds that selectively modulate a level of a subject ethanolamine kinase-encoding nucleic acid molecule, or that selectively modulate a level of a subject protein, or that selectively modulates a level of ethanolamine kinase enzyme activity, are identified as potential pesticide and drug candidates having specificity for the subject protein. Whether a candidate compound selectively modulates a level of a subject ethanolamine kinase-encoding nucleic acid molecule, or selectively modulates a level of a subject protein, or selectively modulates a level of ethanolamine kinase enzyme activity can be determined by measuring the level of an mRNA or protein, e.g., GAPDH, or other suitable control protein or mRNA, where a candidate agent is "selective" if it does not substantially inhibit the production of or activity of any protein or mRNA other than an ethanolamine kinase protein or ethanolamine kinase-encoding mRNA.

Identification of small molecules and compounds as potential pesticides or pharmaceutical compounds from large chemical libraries requires high-throughput screening (HTS) methods (Bolger, Drug Discovery Today (1999) 4:251–253). Several of the assays mentioned herein can lend themselves to such screening methods. For example, cells or cell lines expressing wild type or mutant subject protein or its fragments, and a reporter gene can be subjected to compounds of interest, and depending on the reporter genes, interactions can be measured using a variety of methods such as color detection, fluorescence detection (e.g. GFP), autoradiography, scintillation analysis, etc.

Test agents that reduce ethanolamine kinase activity can then be purified using conventional purification techniques, or can be synthesized de novo by conventional procedures.

Compounds identified using the above-described methods are useful to control pests, e.g., are useful as pesticides. Such compounds can control pests, e.g., by reducing pest growth, and/or fertility, and/or viability. The present invention provides compounds identified using any of the above-described assays. In many embodiments, an agent identified using the instant methods is purified, e.g., is separated from components (e.g., macromolecules and smaller compounds, e.g., down to about 50 Daltons) with which it is naturally associated, or, where the agent exists in a library, is separated from other members of the library. In many embodiments, a purified agent is at least about 50% pure, at least about 70% pure, at least about 80% pure, at least about 90% pure, at least about 95% pure, or at least about 99% pure.

Thus, in some embodiments, the invention provides a method for preparing a pesticidal agent that reduces enzymatic activity of an insect ethanolamine kinase, generally involving identifying a candidate pesticidal agent, as described above; and purifying the agent. In general, a test agent that reduces ethanolamine kinase activity of a subject ethanolamine kinase by at least 20% when compared to a suitable control indicates that the test agent is a candidate pesticidal agent.

Pesticidal Agents Identified using the Subject Screening Methods

The present invention further provides pesticidal agents identified by a screening method of the invention.

Pesticides can be delivered by a variety of means including direct application to pests or to their food source. In addition to direct application, toxic proteins and pesticidal nucleic acids (e.g. dsRNA) can be administered using biopesticidal methods, for example, by viral infection with nucleic acid or by transgenic plants that have been engineered to produce interfering nucleic acid sequences or encode the toxic protein, which are ingested by plant-eating pests.

Putative pesticides, drugs, and molecules can be applied onto whole insects, nematodes, and other small invertebrate metazoans, and the ability of the compounds to modulate (e.g. block or enhance) activity of a subject protein can be observed. Alternatively, the effect of various compounds on a subject protein can be assayed using cells that have been engineered to express one or more subject proteins and associated proteins.

Of particular interest in many embodiments are agents that are selective inhibitors of an insect ethanolamine kinase. "Selective inhibitors" are those agents that inhibit an insect ethanolamine kinase but do not substantially inhibit a ethanolamine kinase from a non-insect species.

A pesticidal composition of the invention comprises an agent that reduces the enzymatic activity of an insect ethanolamine kinase by at least about 10%, at least about 20%, at least about 30%, at least about 40%, at least about 50%, at least about 60%, at least about 70%, or more. In particular, an agent inhibits enzymatic activity of an insect ethanolamine kinase that has at least about 80%, at least about 85%, at least about 90%, at least about 95%, at least about 98%, or more amino acid sequence identity to SEQ ID NO:02 or SEQ ID NO:04. A subject pesticidal composition comprises an agent; and conventional excipients.

Agents that prove to be selective for invertebrate pests are formulated for application to an invertebrate pest population. Active agents can be formulated with an acceptable carrier into a pesticidal composition that is, for example, a suspension, a solution, an emulsion, a dusting powder, a dispersible granule, a wettable powder, an emulsifiable concentrate, an aerosol or impregnated granule. Formulations comprising an active agent identified by a screening method of the invention can be applied directly to plants to protect the plants against damage by an invertebrate pest, can be applied to the soil in which a plant to be protected is grown, or can be applied directly to the pest. Formulations for pesticides are well known in the art, and any known formulation can be used. U.S. Pat. No. 6,180,088 describes foamable aerosol formulations for insecticidal compounds.

Such compositions disclosed above may be obtained by the addition of a surface active agent, an inert carrier, a preservative, a humectant, a feeding stimulant, an attractant, an encapsulating agent, a binder, an emulsifier, a dye, a U.V. protectant, a buffer, a flow agent, or other component to facilitate product handling and application for particular target pests.

Suitable surface-active agents include but are not limited to anionic compounds such as a carboxylate, for example, a metal carboxylate of a long chain fatty acid; an N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate or dioctyl succinate.

Non-ionic surface active agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates or botanical materials such as wood products, cork, powdered corncobs, peanut hulls, rice hulls, and walnut shells.

The compositions of the present invention can be in a suitable form for direct application or as a concentrate or primary powder which requires dilution with a suitable quantity of water or other diluent before application. The pesticidal concentration will vary depending upon the nature of the particular formulation, specifically, whether it is a concentrate or to be used directly. The composition generally contains 1 to 98% of a solid or liquid inert carrier, and 0 to 50%, or 0.1 to 50% of a surfactant. These compositions will be administered at the labeled rate for the commercial product, e.g., about 0.01 lb-5.0 lb per acre when in dry form and at about 0.01 pts-10 pts per acre when in liquid form.

Subject Nucleic Acids as Biopesticides

Subject nucleic acids and fragments thereof, such as antisense sequences or double-stranded RNA (dsRNA), can be used to inhibit subject nucleic acid molecule function, and thus can be used as biopesticides. Methods of using dsRNA interference are described in published PCT application WO 99/32619. The biopesticides may comprise the nucleic acid molecule itself, an expression construct capable of expressing the nucleic acid, or organisms transfected with the expression construct. The biopesticides may be applied directly to plant parts or to soil surrounding the plants (e.g. to access plant parts growing beneath ground level), or directly onto the pest.

Biopesticides comprising a subject nucleic acid may be prepared in a suitable vector for delivery to a plant or animal. For generating plants that express the subject nucleic acids, suitable vectors include *Agrobacterium tumefaciens* Ti plasmid-based vectors (Horsch et al., Science (1984) 233:496–89; Fraley et al., Proc. Natl. Acad. Sci. USA (1983) 80:4803), and recombinant cauliflower mosaic virus (Hohn et al., 1982, In Molecular Biology of Plant Tumors, Academic Press, New York, pp 549–560; U.S. Pat. No. 4,407,956 to Howell). Retrovirus based vectors are useful for the introduction of genes into vertebrate animals (Burns et al., Proc. Natl. Acad. Sci. USA (1993) 90:8033–37).

Transgenic insects can be generated using a transgene comprising a subject gene operably fused to an appropriate inducible promoter. For example, a tTA-responsive promoter may be used in order to direct expression of a subject protein at an appropriate time in the life cycle of the insect. In this way, one may test efficacy as an insecticide in, for example, the larval phase of the life cycle (i.e. when feeding does the greatest damage to crops). Vectors for the introduction of genes into insects include P element (Rubin and Spradling, Science (1982) 218:348–53; U.S. Pat. No. 4,670,388), "hermes" (O'Brochta et al., Genetics (1996) 142:907–914), "minos" (U.S. Pat. No. 5,348,874), "mariner" (Robertson, Insect Physiol. (1995) 41:99–105), and "sleeping beauty" (Ivics et al., Cell (1997) 91(4):501–510), "piggyBac" (Thibault et al., Insect Mol Biol (1999) 8(1):119–23), and "hobo" (Atkinson et al., Proc. Natl. Acad. Sci. U.S.A. (1993) 90:9693–9697).

Recombinant virus systems for expression of toxic proteins in infected insect cells are well known and include Semliki Forest virus (DiCiommo and Bremner, J. Biol. Chem. (1998) 273:18060–66), recombinant sindbis virus (Higgs et al., Insect Mol. Biol. (1995) 4:97–103; Seabaugh et al., Virology (1998) 243:99–112), recombinant pantropic retrovirus (Matsubara et al., Proc. Natl. Acad. Sci. USA (1996) 93:6181–85; Jordan et al., Insect Mol. Biol. (1998) 7:215–22), and recombinant baculovirus (Cory and Bishop, Mol. Biotechnol. (1997) 7(3):303–13; U.S. Pat. Nos. 5,470,735; 5,352,451; 5,770,192; 5,759,809; 5,665,349; and 5,554,592).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Cloning of cDNA Encoding *Heliothis* Ethanolamine Kinase

Two cDNAs homologous to *Drosophila* ethanolamine kinase (EK) were amplified from a *Heliothis virescens* cDNA library, and sequenced in their entireties. The cDNA sequence of a long form is provided in FIG. 1, and the amino acid sequence of the encoded EK is provided in FIG. 2. The cDNA sequence of the short form is provided in FIG. 3, and the amino acid sequence of the encoded EK is provided in FIG. 4.

Expression constructs of the long form EK open reading frame were made and introduced into *E. coli* by transformation. Expression product was purified using column chromatography.

Example 2

Measuring Enzymatic Activity of Ethanolamine Kinase

The following assay measures the depletion of ATP that follows the phosphorylation of ethanolamine by ATP. Remaining ATP is measured biochemically by luciferase, which consumes ATP and emits light. The quantity of emitted light is proportional to the concentration of remaining ATP in the reaction mixture.

Reagents are prepared in a standard assay buffer solution of 0.10 M Tris (USB), pH 8.0 unless otherwise noted. 0.003 mL of ethanolamine (USB) at 2.3 mM admixed with candidate pesticidal agents at varying concentrations dissolved in 5% DMSO is added to microtiter plate wells. Next, 0.01 mL of 270 nM EK (from Example 1) is added. 0.015 mL of substrate is added to each well to initiate the reaction; the substrate is 0.10 mM ATP (Roche) in 20 mM $MgCl_2.6\ H_2O$ (Sigma) 0.1% (w/v) Tween 20 (USB). The plate is inclubated at room temperature for 1 hour. For the luciferase readout, 0.02 mL of the following is added to each well: 20 mM HEPES (USB), pH 7.8, 0.040 oxalic acid (USB), 0.16% (v/v) Triton X-100 (USB), 2.5 mM DTT (USB), 0.13 mM Coenzyme A (USB), 0.040 mM Luciferin (USB), 0.025 mM AMP, and 600 units luciferase (Sigma). Emission of light is detected using a luminometer. Agents that inhibit the EK reaction give an observed increase in light emission relative to negative controls.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for detecting an agent that reduces an enzymatic activity of an insect ethanolamine kinase, said method comprising contacting said ethanolamine kinase or fragment thereof having enzymatic activity with a test agent; and determining the effect, if any, of said test agent on ethanolamine kinase activity of said enzyme or fragment; wherein said ethanolamine kinase comprises an amino acid sequence amino acid sequence set forth in SEQ ID NO:02.

2. The method of claim 1, further comprising selecting a test agent that reduces ethanolamine kinase activity; determining an effect, if any, of the test agent on insect viability, wherein a test agent that reduces insect viability is identified as a pesticidal agent.

3. The method of claim 1, wherein said contacting comprises administering said test agent to cultured host cells that have been genetically engineered to produce said ethanolamine kinase.

4. A method for preparing a pesticidal agent that reduces enzymatic activity of an insect ethanolamine kinase, the method comprising:

contacting a test agent with an insect ethanolamine kinase comprising an amino acid sequence set forth in SEQ ID NO:02;

determining the effect, if any, of said test agent on ethanolamine kinase activity of said ethanolamine kinase, wherein a reduction of ethanolamine kinase activity of at least 20% when compared to a suitable control indicates that the test agent is a candidate pesticidal agent; and purifying the candidate pesticidal agent.

* * * * *